United States Patent
Ringemann et al.

(10) Patent No.: US 11,060,978 B2
(45) Date of Patent: Jul. 13, 2021

(54) METHODS OF DETERMINING AN ANALYTE CONCENTRATION IN A BODY FLUID SAMPLE HAVING DISTURBANCE VARIABLES, AS WELL AS COMPUTER PROGRAMS AND DEVICES THEREFOR

(71) Applicant: Roche Diabetes Care, Inc., Indianapolis, IN (US)

(72) Inventors: Christian Ringemann, Mannheim (DE); Markus Plum, Mainz (DE); Wolfgang Petrich, Bad Schoenborn (DE); Timo Ottenstein, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 565 days.

(21) Appl. No.: 14/745,023

(22) Filed: Jun. 19, 2015

(65) Prior Publication Data

US 2016/0011120 A1 Jan. 14, 2016

Related U.S. Application Data

(63) Continuation of application No. PCT/EP2013/077363, filed on Dec. 19, 2013.

(30) Foreign Application Priority Data

Dec. 20, 2012 (EP) ..................................... 12198443

(51) Int. Cl.
   *G01N 21/84* (2006.01)
   *G16C 20/70* (2019.01)
   (Continued)

(52) U.S. Cl.
   CPC ......... *G01N 21/8483* (2013.01); *G16C 20/70* (2019.02); *C12Q 1/54* (2013.01);
   (Continued)

(58) Field of Classification Search
   CPC ........ C12Q 1/54; G01N 21/274; G01N 33/66; G01N 21/8483; G01N 2201/129; G01N 2201/12; G06F 19/707
   (Continued)

(56) References Cited

U.S. PATENT DOCUMENTS

| 5,168,046 A | 12/1992 | Hamamoto et al. |
| 5,420,042 A | 5/1995 | Schafer et al. |

(Continued)

FOREIGN PATENT DOCUMENTS

| EP | 0302287 A2 | 2/1989 |
| EP | 0354441 A2 | 2/1990 |

(Continued)

OTHER PUBLICATIONS

Hones, et al., The Technology Behind Glucose Meters: Test Strips, Diabetes Technology & Therapeutics, vol. 10, Supplement 1, 2008.

*Primary Examiner* — Rebecca M Fritchman
(74) *Attorney, Agent, or Firm* — Stinson LLP

(57) ABSTRACT

Methods are provided for deriving/determining an analyte concentration that include recording measurement values during a time development indicating a progress of a detection reaction of at least one test substance and a body fluid sample and providing at least one measurement curve F(t) containing the measurement values, where the detection reaction is known to be influenced by the analyte concentration and at least one disturbance variable Y. The methods also include deriving an end value of the measurement curve to form a first variable $x_1$, and deriving at least one fit parameter by taking into account an exponential characteristic of the measurement curve, and where the fit parameter forms at least one second variable $x_2$. The methods further include deriving/determining the analyte concentration by using at least one multivariate evaluation algorithm adapted to combine $x_1$ and $x_2$. Also provided are computer programs and devices that incorporate the same.

21 Claims, 16 Drawing Sheets

(51) Int. Cl.
  *G01N 21/27* (2006.01)
  *G01N 33/66* (2006.01)
  *C12Q 1/54* (2006.01)

(52) U.S. Cl.
  CPC ........... *G01N 21/274* (2013.01); *G01N 33/66* (2013.01); *G01N 2201/12* (2013.01); *G01N 2201/129* (2013.01)

(58) Field of Classification Search
  USPC ............................... 436/95, 164; 422/82.05
  See application file for complete search history.

(56) References Cited

U.S. PATENT DOCUMENTS

| | | |
|---|---|---|
| 6,448,067 B1 | 9/2002 | Tajnafoi |
| 2002/0146835 A1 | 10/2002 | Modzelewski et al. |
| 2008/0070234 A1 | 3/2008 | Spinke et al. |
| 2008/0087819 A1 | 4/2008 | Kalveram et al. |
| 2008/0118942 A1 | 5/2008 | Sugiyama et al. |
| 2010/0075433 A1 | 3/2010 | Porsch et al. |
| 2010/0270178 A1 | 10/2010 | Guo et al. |
| 2011/0315564 A1 | 12/2011 | Guthrie et al. |
| 2014/0078149 A1 | 3/2014 | Coombes et al. |
| 2014/0322703 A1 | 10/2014 | Spinke et al. |
| 2015/0121006 A1 | 4/2015 | Dong et al. |

FOREIGN PATENT DOCUMENTS

| | | |
|---|---|---|
| EP | 0431456 A1 | 6/1991 |
| EP | 0547710 A2 | 6/1993 |
| EP | 0821234 B1 | 1/1998 |
| EP | 1413883 A1 | 4/2004 |
| EP | 1593434 A2 | 11/2005 |
| JP | H0344555 A | 2/1991 |
| JP | H06167501 A | 6/1994 |
| JP | H06201585 A | 7/1994 |
| JP | 2005327906 A | 11/2005 |
| JP | 2008070366 A | 3/2008 |
| JP | 2006046538 A1 | 5/2008 |
| JP | 2009501316 A | 1/2009 |
| JP | 2012008151 A | 1/2012 |
| JP | 2012037332 A | 2/2012 |
| WO | 199918426 A1 | 4/1999 |
| WO | 0125760 A1 | 4/2001 |
| WO | 2006138226 A2 | 12/2006 |
| WO | 2007012494 A1 | 2/2007 |
| WO | 2009103540 A1 | 8/2009 |
| WO | 2010094426 A1 | 8/2010 |
| WO | 2010094427 A2 | 8/2010 |
| WO | 2011012269 A2 | 2/2011 |
| WO | 2011012270 A1 | 2/2011 |
| WO | 2011012271 A2 | 2/2011 |
| WO | 2011131490 A1 | 2/2011 |
| WO | 2011061257 A1 | 5/2011 |

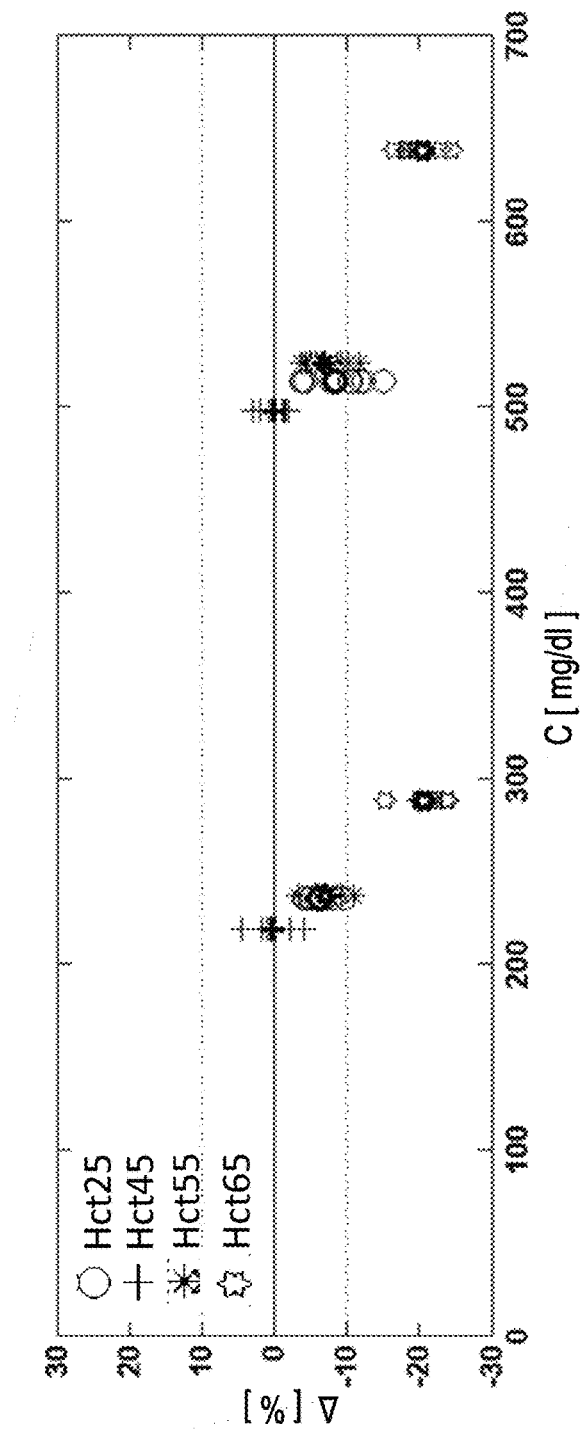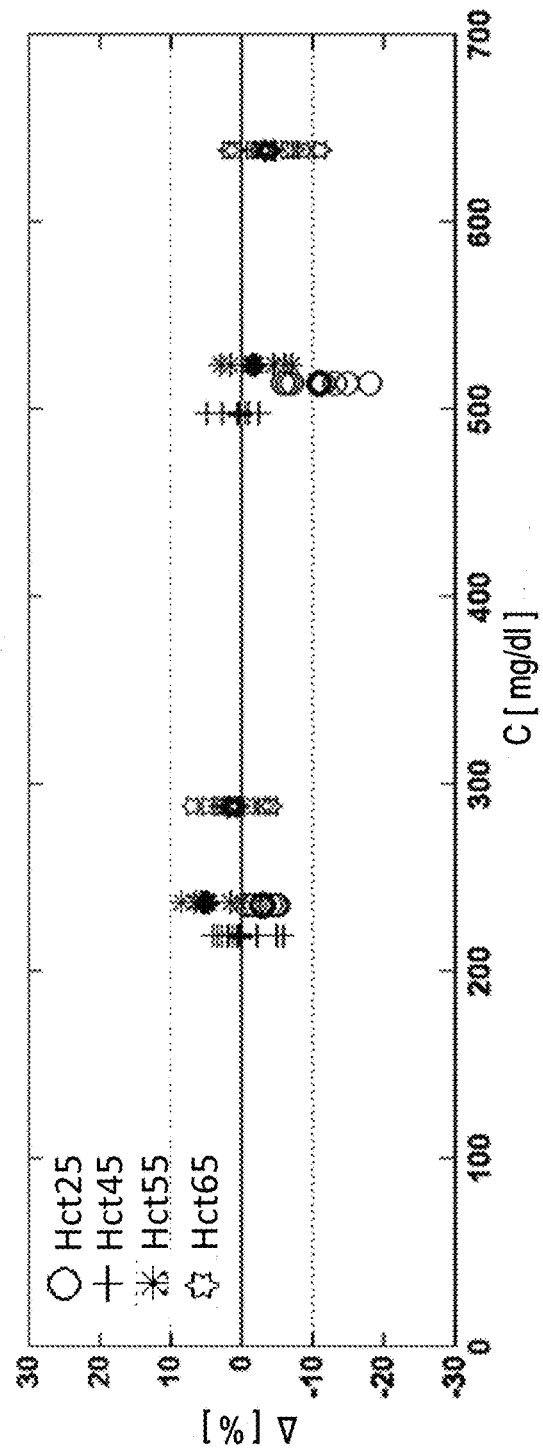

METHODS OF DETERMINING AN ANALYTE CONCENTRATION IN A BODY FLUID SAMPLE HAVING DISTURBANCE VARIABLES, AS WELL AS COMPUTER PROGRAMS AND DEVICES THEREFOR

CROSS-REFERENCE TO RELATED APPLICATIONS

This patent application is a continuation of Int'l Patent Application No. PCT/EP2013/077363; filed 19 Dec. 2014, which claims priority to and the benefit of EP Patent Application No. 12198443.9; filed 20 Dec. 2012. Each patent application is incorporated herein by reference as if set forth in its entirety.

JOINT RESEARCH AGREEMENT

The present disclosure was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are 1) Roche Diagnostics GmbH and. and 2) Dioptic GmbH.

TECHNICAL FIELD

This disclosure relates generally to mathematics and medicine/medical diagnostics, and more particularly, it relates to methods of determining an analyte concentration in a body fluid sample having or suspected of having one or more disturbance variables, as well as computer programs and evaluation devices/systems for analyzing at least one body fluid sample for an analyte of interest that incorporate the same.

BACKGROUND

A large number of methods and devices for determining one or more analytes in body fluids are known. Without restricting the scope of the present disclosure, in the following, reference is made mainly to determining blood glucose concentrations.

For performing fast and simple measurements, several types of test elements are known that are based on using a test substance (i.e., using one or more chemical compounds or chemical mixtures adapted for performing a detection reaction) for detecting an analyte of interest. The test substance also can be referred to as the "test chemistry." For details of potential test substances, which may be used herein, reference may be made to Hoenes et al. (2008) *Diabetes Technol. Ther.* 10:S10-S26, as well as Int'l Patent Application Publication Nos. WO 2007/012494, WO 2009/103540, WO 2010/094426, WO 2010/094427, WO 2011/012269, WO 2011/012270 and WO 2011/012271. Additional reference may be made to EP Patent Application Publication Nos. 0 354 441, 0 431 456, 0 302 287, 0 547 710 and 1 593 434 for test substances that may be used herein. Other types of test elements and/or test substances are feasible and may be used herein.

By using one or more test substances, a detection reaction may be initiated, the course of which depends on the concentration of the analyte of interest. For deriving the analyte concentration, progress of the detection reaction may be monitored by measuring and/or monitoring a time development of at least one measurement value indicating the progress of the detection reaction. This measurement value generally may be an arbitrary measurement value linked to the detection reaction, such as an optical measurement value. For example, in many measurement setups, optical measurement values are monitored, such as a remission of a test field containing the test substance. By recording the time development of at least one measurement value, a measurement curve is provided.

A major challenge resides in a fast, reliable and precise determination of the analyte concentration from the measurement curve. For this purpose, a large number of methods and devices are known in the art. For example, EP Patent No. 0 821 234 and US Patent Application Publication No. 2002/0146835, disclose methods and devices in which the measurement curve is directly or indirectly compared with one or more thresholds. Specifically, EP Patent No. 0 821 234 discloses a method in which a slope of the measurement curve is determined by deriving difference values of colors and comparing these difference values with a predetermined threshold. Thereby, an end point of the detection reaction may be determined.

Similarly, in US Patent Application No. 2002/0146835 discloses an end point is determined by calculating an intermediate analyte level of the testing element at predetermined intervals and calculating a ratio value corresponding to the (n)th measurement to an (n−5)th measurement. When two consecutive ratio values are less than or equal to a predetermined value, the end point is deemed to be reached, and the final analyte level can be determined.

Further, several methods and devices for using one or more fitting algorithms are known in the art, in which the measurement curve is analyzed by using one or more fit functions. For example, Int'l Patent Application Publication No. WO 2011/061257 discloses a method and a device for analyzing a body fluid, in which a photometric measurement curve is measured. A transmission behavior of an optical transmission system is controlled by detecting measured values at two different measurement wavelengths. Further, fit functions are generated for the two measurement curves and by extrapolating fit curves, an offset of the measurement values is determined.

Likewise, US Patent Application Publication No. 2008/0087819 discloses a method for analyzing a fluid sample in which, again, two different wavelengths are used for deriving two measurement curves. The measurement curves are fitted by using an exponential rise with a subsequent exponential fall, by performing an appropriate fit algorithm having two different types of temporal constants.

Moreover, Int'l Patent Application Publication No. WO 2001/025760 discloses a timing-independent method of determining a proper time for measuring a reaction between a sample fluid and a reagent on an analyte strip. A measurement curve of a characteristic of a matrix, to which sample fluid is applied, is periodically measured both before and after applying the sample fluid. Subsequently, a transformation is made of the measurement curve into a function that is independent in time or at most various linearly in time. The second derivative of the transformed function then is analyzed to determine when the second derivative falls below a predetermined threshold. At this point in time, the transformed function will yield the analyte concentration in the sample fluid.

Furthermore, EP Patent Application Publication No. 1 413 883 discloses a method of reducing analysis time of end point-type reaction profiles. A detection reaction is initiated, obtaining at least three measurements, at three different points in time, of a value or level of an observable associated with the detection reaction. Subsequently, an end point value for the observable is estimated from the measurements, by using an appropriate fit function.

Int'l Patent Application Publication No. WO 2006/138226 discloses an arrangement and an algorithm for calculating an analyte concentration contained in a fluid sample. A color change rate of a test chemical is detected, and a hematocrit (Hct) is derived from the color change rate. An appropriate correction factor indicative of Hct is used for correcting a glucose concentration.

Int'l Patent Application Publication No. WO 1999/018426 also discloses a method and a device for analyzing an analyte concentration in a fluid sample, particularly glucose content in a blood sample. The analyte concentration in the fluid sample is determined by screening the color reaction of a test strip over time by means of optical reflectance, where linear functions or polynoms are employed for evaluation purposes.

While significantly improving reliability and reproducibility of analyte detection, these known methods may be improved in various ways. Thus, firstly, most of the fitting algorithms as known in the art are rather complicated and involve a high consumption of electrical power, hardware and software resources and evaluation time. Specifically when using hand-held devices, these aspects may lead to significant disadvantages.

Further, many of the known methods and devices are susceptible to irritations and malfunctions, such as offsets, jitters or discontinuities in the measurement curves. In view of such disturbances and artifacts, which may be due to various boundary conditions of the fluid sample itself, the measurement conditions and the measurement device may impede an analytical evaluation and, in a worst case, may lead to imprecise measurement results.

Specifically, many of the known methods and devices are not suited to take into account that the detection reaction itself may be influenced by one or more disturbance variables other than the analyte concentration itself. In many test elements, a concentration of particulate components in the fluid sample may have a significant impact on the measurement results. For example, the concentration of cellular components, such as blood cells (e.g., Hct), is known to have an influence on the analyte concentration as determined by standard test elements, such as glucose test strips. This influence may be due to sample propagation properties, as well as diffusion processes that are significantly altered by particulate components such as blood cells. Besides Hct, other disturbance variables are known, such as the temperature of the sample and/or the measurement system. As mentioned above, known methods and devices often are not suited to take into account these disturbance variables when evaluating measurement curves for the purpose of determining the analyte concentration.

For the foregoing reasons, there is a need for methods and devices that at least partially overcome the disadvantages and challenges of known methods and devices. Specifically, methods and devices shall be disclosed that are suited to determine one or more analyte concentrations in a body fluid such as blood in a simple and, still, reliable fashion, taking into account disturbances that may have an impact on a detection reaction.

BRIEF SUMMARY

An inventive concept described herein includes deriving an analyte concentration in a body fluid sample despite the presence of one or more disturbance variables that may have an influence or impact on the detection reaction from which a the analyte concentration is determined. Briefly, the inventive concept is achieved by using a first variable $x_1$ indicating an end value of a measurement curve and, additionally, using at least one fit parameter derived by assuming an exponential characteristic of the measurement curve or at least an evaluation part thereof as at least one second variable $x_2$, which subsequently can be used to derive the analyte concentration. The inventive can be incorporated into exemplary methods, computer programs, evaluation devices and systems as described herein.

For example, methods are disclosed for deriving an analyte concentration in a body fluid sample having (or suspected of having) at least one disturbance variable. Briefly, the methods can include the following steps:

Step (a): recording a plurality of measurement values by monitoring a time development of at least one measurement value indicating a progress of a detection reaction of at least one analyte of interest and the body fluid sample, and providing at least one measurement curve F(t) having the measurement values, where at least an evaluation part of the at least one measurement curve has an exponential characteristic, where the measurement values are acquired at differing points in time, where the detection reaction is influenced by an analyte concentration c of the analyte to be detected in the body fluid sample and at least one disturbance variable Y;

Step (b): deriving an end value of the measurement curve, where the end value forms a first variable $x_1$;

Step (c): deriving at least one fit parameter from the at least one measurement curve by taking into account the exponential characteristic of at least the evaluation part of the measurement curve, where the fit parameter forms at least one second variable $x_2$; and Step (d): deriving the analyte concentration c by using at least one multivariate evaluation algorithm, where the multivariate evaluation algorithm combines the first variable $x_1$ and the second variable $x_2$.

Alternatively, the methods can include the following steps:

Step (a'): providing at least one measurement curve F(t), where the measurement curve contains a plurality of measurement values recorded by monitoring a time development of at least one measurement value indicating a progress of a detection reaction of at least one test substance and the body fluid sample, where the measurement values contained in the measurement curve are acquired at differing points in time, where the detection reaction is known to be influenced by an analyte concentration c to be detected in the body fluid sample and at least one disturbance variable Y;

Step (b'): deriving an end value of the measurement curve, where the end value forms a first variable $x_1$;

Step (c'): deriving at least one fit parameter from the measurement curve by assuming an exponential characteristic of at least an evaluation part of the measurement curve, where the fit parameter forms at least one second variable $x_2$; and Step (d'): deriving the analyte concentration c by using at least one multivariate evaluation algorithm, the multivariate evaluation algorithm being adapted to combine the first variable $x_1$ and the second variable $x_2$.

In some instances, the body fluid can be blood (such as whole blood) or interstitial fluid. In other instances, one or more other body fluids may be used such as, for example, urine and/or saliva.

With respect to the analyte, it can be an arbitrary analyte that may be present in the body fluid. In general, the analyte is a metabolite and/or takes part in the metabolism of a human or an animal. In some instances, the analyte is glucose. In other instances, other analytes may be detected such as, for example, lactate and/or triglycerides.

With respect to the test substance, it can be at least one enzyme. In some instances, the test substance is a glucose oxidase (GOD) and/or a glucose dehydrogenase (GDH).

In some instances, the measurement values are optical measurement values such as, for example, a reflective measurement. In other instances, the measurement values are remission values.

With respect to the at least one disturbance variable Y, it can include a parameter that can influence the viscosity of the body fluid. In some instances, the at least one disturbance variable can be a particulate content of the sample, such as a Hct or a temperature of the sample.

In some instances, and with respect to step (b) or (b'), a slope of the measurement curve can be compared to at least one threshold value for determining if the measurement curve has reached the end value. Difference values of neighboring measurement values of the measurement curve can be formed and compared to the at least one threshold value.

In some instances, and with respect to step (b) or (b'), the end value is derived from at least one measurement value of the measurement curve and, in step (c) or (c'), the at least one second variable is derived from at least one fit parameter from the measurement curve. The end value can be derived from an earlier part of the measurement curve, where the earlier part is a part of the measurement curve being distant from a plateau of the measurement curve. Moreover, every measurement curve may form a same plateau value independent from the at least one disturbance variable Y. Alternatively, the end value may be determined from the same part of the measurement curve in which the decay constant $\Gamma$ or a quantity related to the decay constant $\Gamma$ may be determined as the second variable $x_2$.

Regardless, the evaluation part of the measurement curve can be a remainder of the measurement curve starting after a definable starting time span after a commencement of a measurement, where the starting time span is a predetermined time span. In some instances, the predetermined time span is about 0.5 s to about 3 s, about 1.0 s to about 2.0 s, or about 1.5 s to about 1.7 s.

In some instances, the multivariate evaluation algorithm is determined by using a plurality of calibration measurements.

In some instances, the exponential characteristic contains at least one exponential function selected from:

$$F(t)=a+b*\exp[-*t],$$

where t is the time, a is an offset, b is a contrast, and $\Gamma$ is a decay constant; and $$F(t)=a+b*\exp[-(\Gamma*t)^\beta],$$

where t is the time, a is an offset, b is a contrast, $\Gamma$ is a decay constant and $\beta$ is a stretching parameter.

In some instances, the second variable $x_2$ can be the decay constant $\Gamma$ or from a quantity that is in relationship with the decay constant $\Gamma$. In other instances, the quantity is proportional to the decay constant $\Gamma$ or proportional to the inverse $1/\Gamma$ of the decay constant.

In some instances, in step (c) or (c'), a first order derivative $F'(t)$ or a higher order derivative $F_n(t)$ of the measurement curve is formed before deriving the fit parameter.

In some instances, the measurement values of the measurement curve are acquired equally spaced in time. For example, the wherein the measurement curve can be acquired at a constant measurement frequency of about 10 Hz to about 100 Hz. In this manner, first or higher order derivative can be approximated by calculating differences between neighboring measurement values.

In some instances, in step (c) or (c'), a ratio of two subsequent derivatives $F_n(t)$ and $F_{n+1}(t)$ of the measurement curve is formed, the ratio forming the fit parameter.

In some instances, in step (c) or (c'), an integral is formed over the measurement curve $F(t)$ or a first order or higher order derivative of $F(t)$, the integral forming the fit parameter. In other instances, the fit parameter is obtained by comparing a first order derivative of the measurement curve at two differing points in time, where the two differing points in time can be obtained by applying two differing threshold values. At least one of the two differing points in time can be obtained by a linear interpolation between two differing values that are in the vicinity of a threshold value.

Alternatively, two differing values for the two differing points in time can be used, where each of the two differing values are in the vicinity of a threshold value. Accordingly, the two differing threshold values can be in a range from about −10%/s to about −0.1%/s or in a range from about −5%/s to about −2%/s. Alternatively still, the two differing threshold values can be a preliminary estimation of the body fluid concentration. Therefore, and in certain instances, the body fluid includes glucose, and the preliminary estimation of the body fluid concentration leads to a value of or above about 100 mg/dl, and where the two differing threshold values are about −5%/s and about −2%/s. Is still additional instances, the body fluid includes glucose, and the preliminary estimation of the glucose concentration leads to a value below 100 mg/dl, and the two differing threshold values are about −2%/s and about −0.5%/s.

In some instances, and where the body fluid includes glucose, a Hct correction is applied to the glucose concentration. In other instances, the Hct correction is applied to the glucose concentration when the Hct is outside a predetermined Hct range such as, for example from about 35% to about 50%.

In some instances, and in step (d) or (d'), the at least one disturbance variable Y value is determined.

In some instances, and in step (d) or (d'), a weighted average of results of at least two procedures based on variations of the at least one disturbance variable Y are provided to derive a value for the analyte concentration c, where the weighted average can include weights that denote probabilities for each specific value of the at least one disturbance variable Y. Alternatively, a forecast model can be use and can provide a probability distribution of each specific value of the at least one disturbance variable Y.

The steps may be performed in the given order. However, other orders of the method steps are feasible. Further, one or more or even all of the method steps may be performed repeatedly, by repeating one of the method steps, more than one of the method steps or even all of the method steps once, twice or even more than twice. Further, two or more of the method steps may overlap in time, by performing two or more of these method steps at least partially simultaneously. As will further be outlined in detail below, one of the method steps, a plurality of the method steps, or even all of the method steps may be performed by using a data processing device such as a computer, a microcomputer and/or an application-specific integrated circuit (ASIC).

In view of the foregoing, computers or computer networks are provided that include at least one processor adapted to perform a method as described herein.

Additionally, computer programs or computer loadable data structures are provided that can include computer-executable instructions for performing a method as described herein when the program or data structure is executed on a computer or computer network.

In some instances that computer program is stored on a storage medium readable to a computer, where the a storage medium includes a data structure stored thereon and where the data structure is adapted to perform a method as described herein after having been loaded into a main and/or working storage of a computer or of a computer network.

Also provided are computer program products having program code means, where the program code means can be stored or are stored on a storage medium for performing a method as described herein, if the program code means are executed on a computer or on a computer network.

Likewise, devices are provided that can include evaluation devices for analyzing at least one body fluid sample, where the evaluation devices includes at least one evaluation unit. The evaluation unit can be adapted to perform a method as described herein.

Alternatively, the devices can include sample analysis devices for analyzing a body fluid sample, where the sample analysis devices include at least one measuring unit for measuring a detection reaction of at least one test substance and at least one sample of a body fluid, where the detection reaction is known to be influenced by a set of disturbance variables, each disturbance variable characterizing at least one of a state of the sample of the body fluid and a condition of the detection reaction, the measuring unit further being adapted for monitoring a time development of at least one measurement value indicating a progress of the detection reaction, thereby recording a measurement curve F(t) containing a plurality of the measurement values acquired at different points in time, wherein at least an evaluation part of the measurement curve has an exponential characteristic. The sample analysis devices also include at least one evaluation device.

In some instances, the sample analysis devices include at least one test element, such as at least one test strip, where the test element includes at least one test substance adapted to perform the detection reaction, and where the sample analysis device is adapted such that the body fluid sample is applicable to the test element.

In some instances, the sample analysis device is a handheld device.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 11A shows residuals or deviations of the measured glucose concentration from the actual glucose concentration for uncorrected, univariate measurements.

FIG. 11B shows residuals or deviations of the measured glucose concentration from the actual glucose concentration for corrected, multivariate measurements.

Corresponding reference characters indicate corresponding parts throughout the several views of the drawings.

Figure 1:
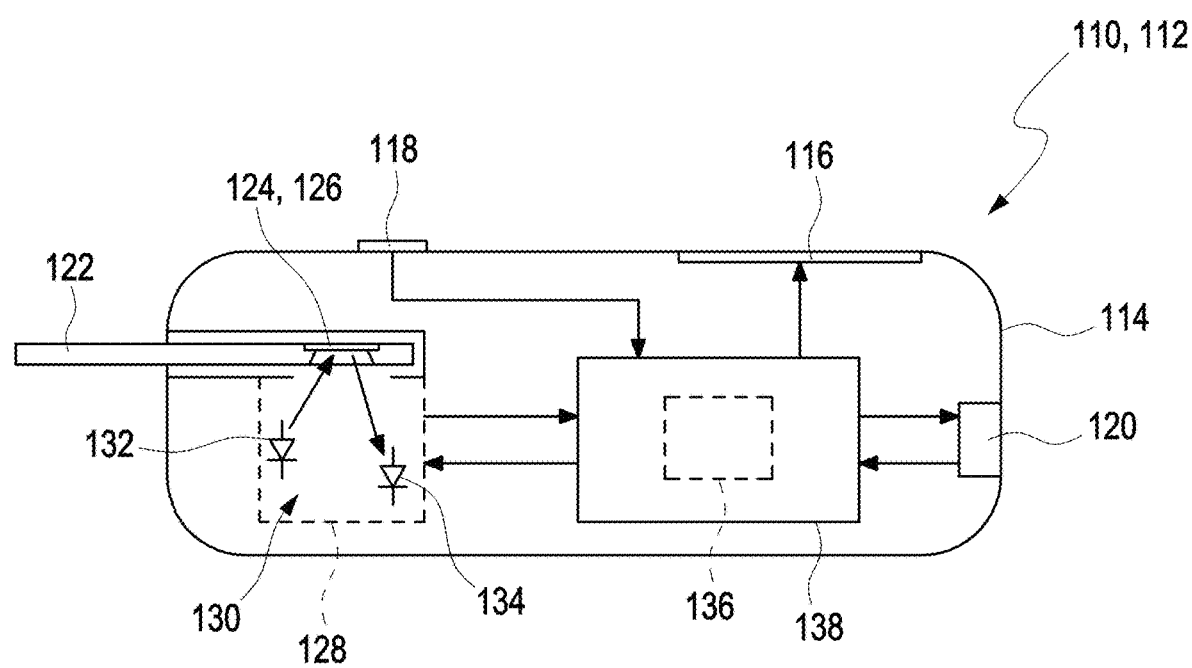
FIG. 1 shows an exemplary sample analysis device in a cross-sectional view.
Figure 2:
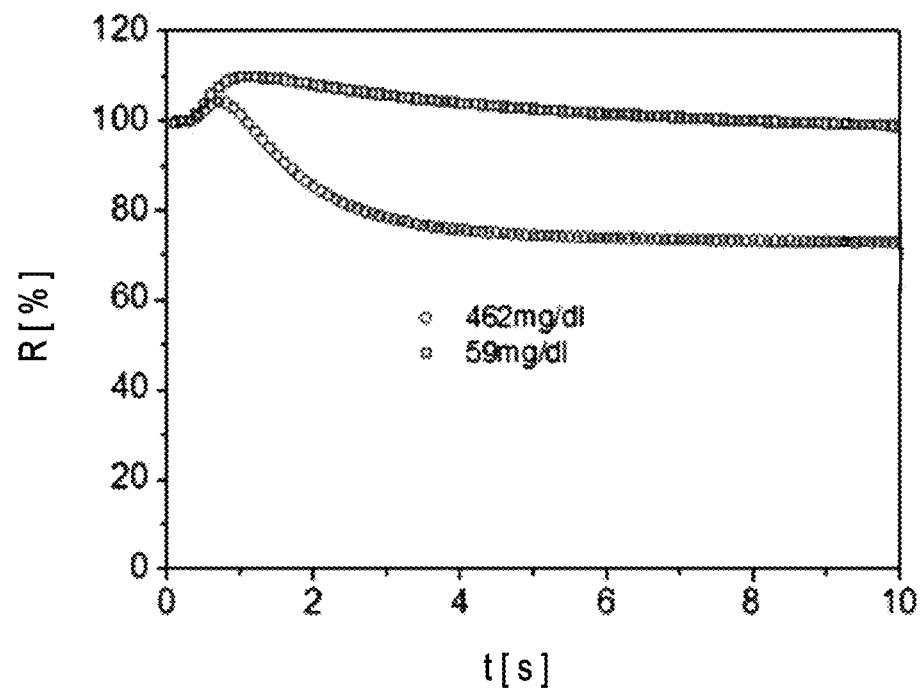
FIG. 2A shows measurement curves of a remission of a first test substance for two different glucose concentrations.
FIG. 2B shows first order derivatives of the measurement curves in FIG. 2A.
Figure 2:
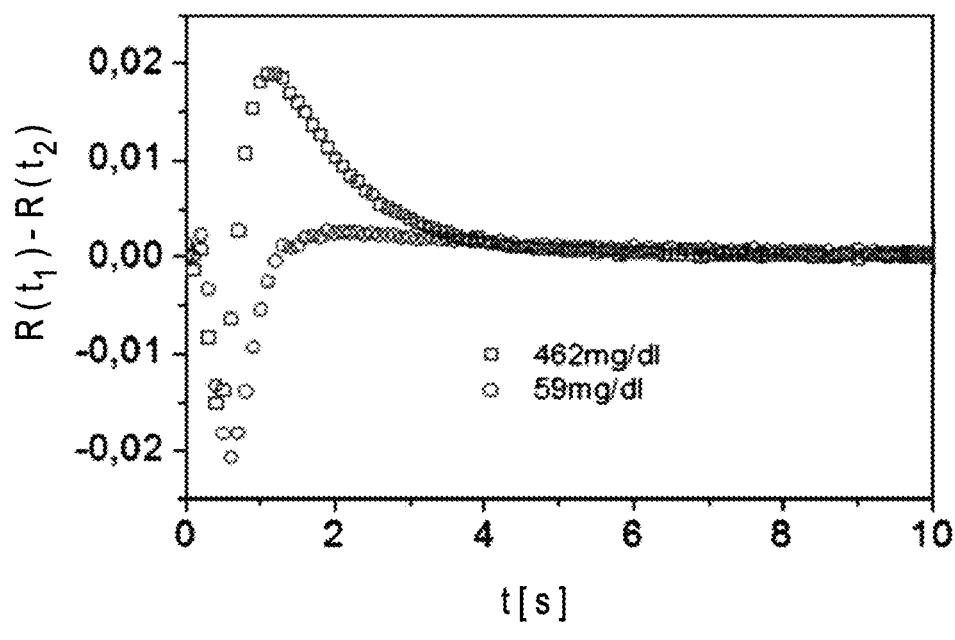
Figure 3:
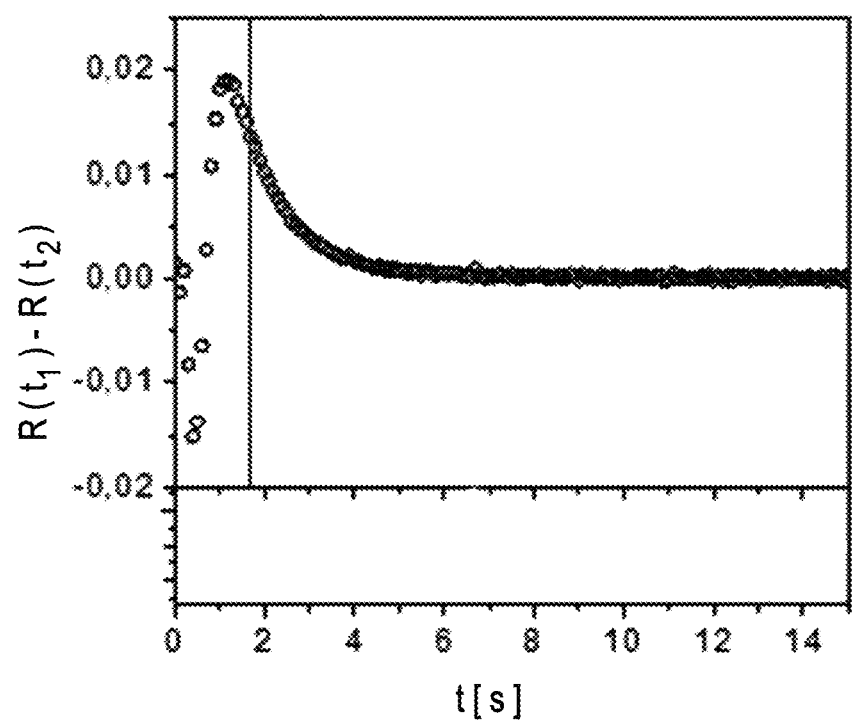
FIG. 3A shows the exponential fit for the first order derivative measurement curve for c=462 mg/dl given in FIG. 2B.
FIG. 3B shows the exponential fit for the first order derivative measurement curve for c=59 mg/dl given in FIG. 2B.
Figure 3:
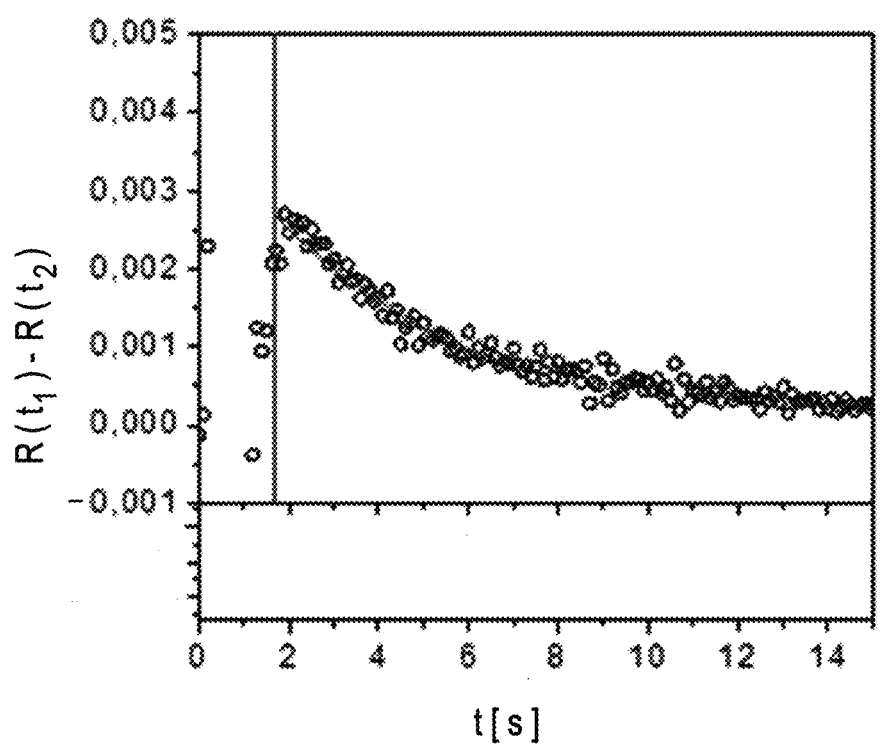
Figure 4:
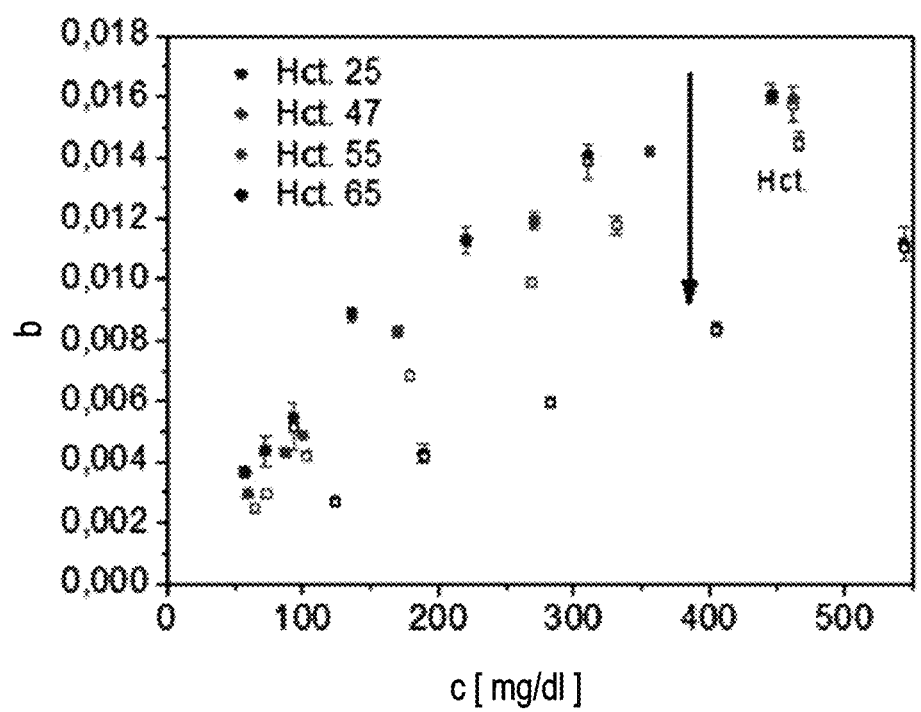
FIG. 4A shows an impact of Hct on the contrast b fit parameter in the fit functions in FIGS. 3A and 3B.
FIG. 4B shows an impact of Hct on the decay rate $\Gamma$ fit parameter in the fit functions in FIGS. 3A and 3B.
Figure 4:
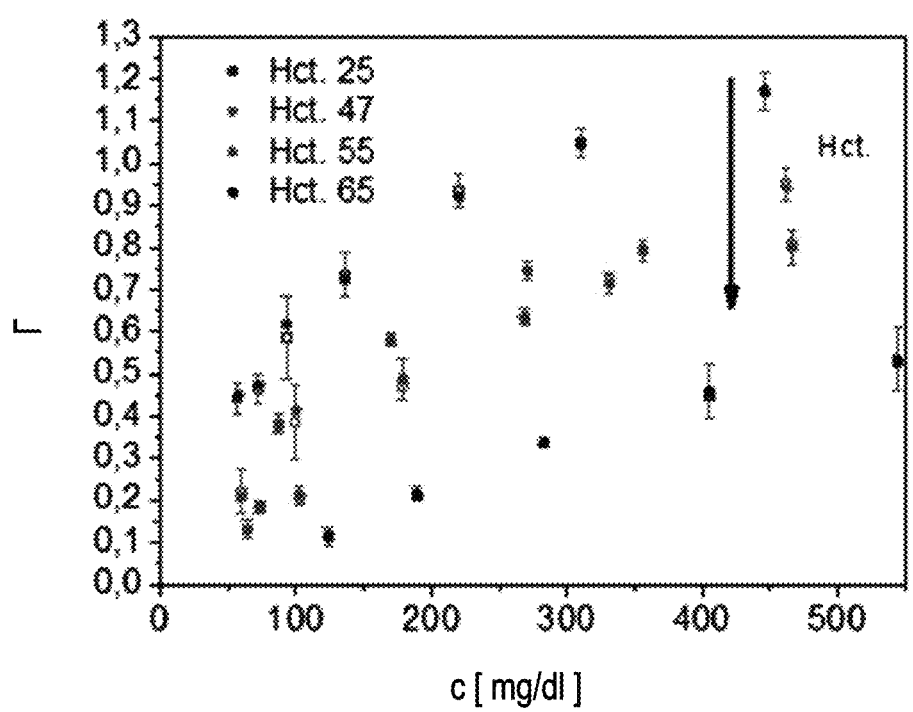
Figure 5:
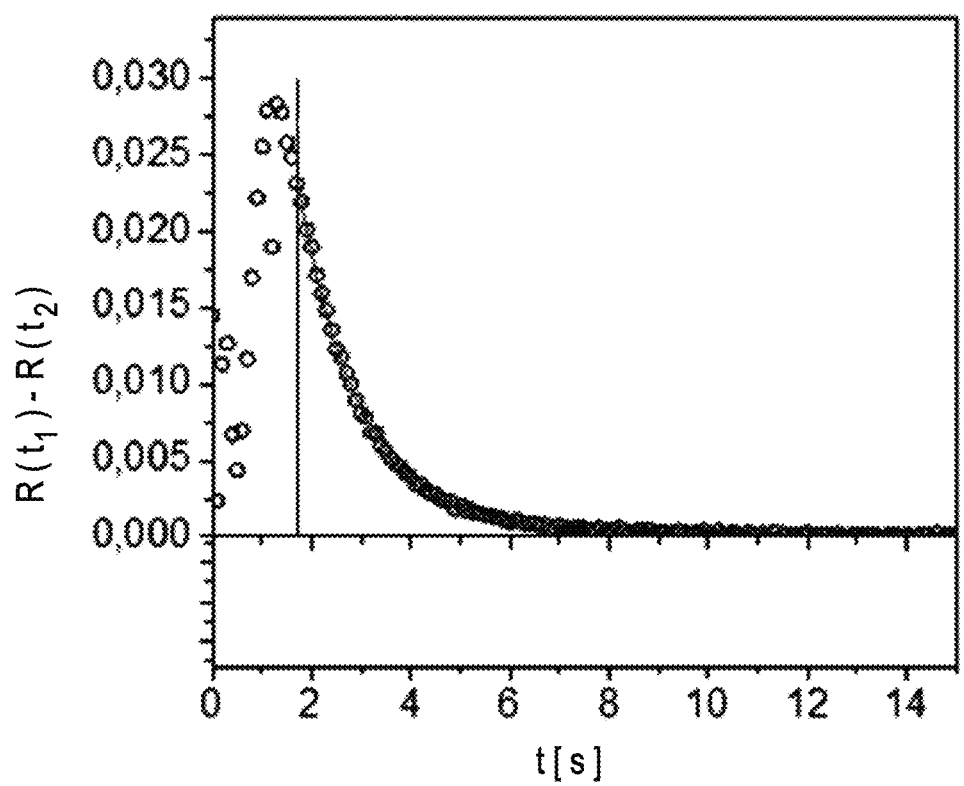
FIG. 5A shows fit functions of first order derivatives in analogy to the fit curve of FIG. 3A.
FIG. 5B shows fit functions of first order derivatives in analogy to the fit curve of FIG. 3B.
Figure 5:
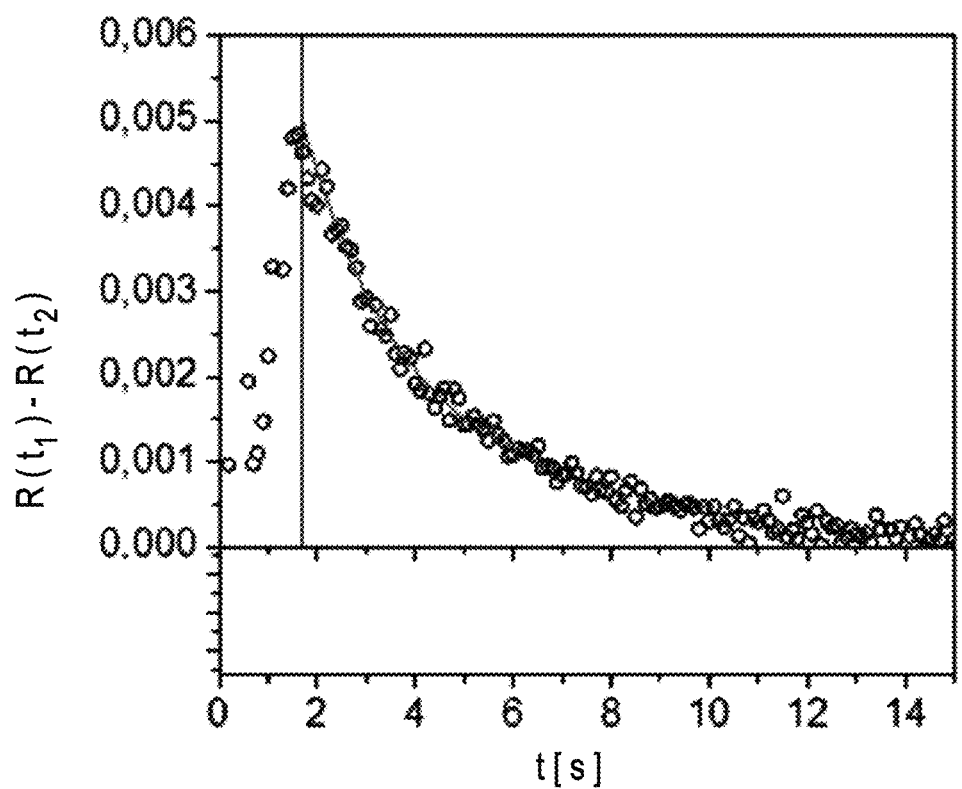

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, computer programs and devices now will be described more fully hereinafter with reference to the accompanying drawings, in which some, but not all embodiments of the inventive concept are shown. Indeed, the methods, computer programs and devices may be embodied in many different forms and should not be construed as limited to the embodiments set forth herein; rather, these embodiments are provided so that this disclosure will satisfy applicable legal requirements.

Likewise, many modifications and other embodiments of the methods, computer programs and devices described herein will come to mind to one of skill in the art to which the disclosure pertains having the benefit of the teachings presented in the foregoing descriptions and the associated drawings. Therefore, it is to be understood that the methods, computer programs and devices are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, computer programs and devices, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

As outlined above or as will be outlined in further detail below, the methods disclosed herein are highly efficient and are adapted to generate measurement results such as the analyte concentration and, optionally, the at least one disturbance variable Y, rather quickly and, still, precisely. Moreover, the methods can be readily adapted for use in small, portable devices which, typically, are rather limited with regard to their hardware and software resources. Therefore, the devices disclosed herein may be embodied as hand-held devices. As used herein, "hand-held device" means a device that is portable by a user, such as in one hand. Typically, the hand-held device may be a device having a volume of less than 1000 cm$^3$ or even less than 500 cm$^3$. Likewise, the weight of the hand-held device is less than 1 kg or even less than 500 g.

The methods, computer programs and devices disclosed herein provide a large number of advantages over known methods, computer programs and devices. Thus, as will be outlined in further detail below, the general concept of using a first variable $x_1$ indicating the end value of the measurement curve and, additionally, using at least one fit parameter derived by assuming an exponential characteristic of the measurement curve or at least an evaluation part thereof as at least one second variable $x_2$, allows for a multiplicity of evaluation options, which are easily implemented.

Thus, as a first option, a simple exponential function may be fitted to the measurement curve, thereby deriving at least one fit parameter, to be used as the additional, second variable $x_2$.

As a second option, a first order or higher order derivative of the measurement curve may be used and may be fitted, whereby, as is evident from equations (1) to (4) below, the offset of the measurement curve may be eliminated.

As a third option, as also evident from the potential fit functions indicating the exponential characteristic above, specifically when considering equation (1) given above, the option of forming a quotient of two subsequent derivatives of the fit function may provide an easy algorithm for determining the parameter $\Gamma$, which may indicate a decay rate or an increase rate of the exponential characteristic.

As a fourth option, as also evident by using one or more of the equations (1) to (4) given above, specifically equation (1), an integration from 0 to ∞ may lead to a simple, constant quotient $b/\Gamma$, wherein b is the contrast of the exponential characteristic, and $\Gamma$ is the decay constant.

As a fifth option, two separate equations for the first derivative of equation (1), wherein the base line may be neglected (a=0), may be set up for two differing threshold values, wherein the parameter $\Gamma$, which may indicate a decay rate and may be obtained from the two equations by a rearranging of the equations and a subsequent substitution. Hereby, the two differing threshold values may be particularly selected from a range from about −10%/s to about −1%/s or from about −5%/s to about −2%/s.

As used herein, "about" means within a statistically meaningful range of a value or values such as, for example, a stated concentration, length, width, height, angle, weight, molecular weight, pH, sequence identity, time frame, temperature, value or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The five options, which may be applied individually or which may be used in arbitrary combination, thus may lead to a simple, efficient generation of at least one fit parameter or additional variable $x_2$, which may be used for the multivariate analysis of the measurement curve.

Thus, by combining the end value and a fit parameter, an efficient and, still, precise algorithm may be provided, which is adapted for correcting the concentration c for a current Hct. As will further be presented, the methods have been shown to be particularly suited for a correction of the glucose concentration by considering the current Hct under which the amount of glucose may be determined when analyzing a body fluid sample such as a blood sample. By taking into account an exponential characteristic for the measurement curve or a derivative thereof, the information contained in the measurement curve, such as in a chemical kinetic remission curve, may be reduced to a few fit parameters, such as to the above-mentioned offset a, the contrast b and the decay rate F. The behavior of these parameters with regard to disturbance variables such as Hct, temperature or relative humidity may be used to generate a corrected analyte concentration and/or for correcting a raw value of the analyte concentration. Within this regard, it may be explicitly mentioned that knowledge of the disturbance variables may not be required for accurately determining the analyte concentration by employing the methods disclosed herein.

In addition to the end value, one or more additional variables $x_2$, such as one or more of the fit parameters a, b, $\Gamma$, $\beta$ or any combination thereof, may be used for improving the measurement result of determining the analyte concentration. Thus, the assumption of an exponential characteristic of at least the evaluation part of the measurement curve or a derivative thereof may lead to a significant data reduction, since the overall amount of data of the measurement curve may be reduced to one fit parameter and/or a set of a few fit parameters. This feature may be useful to reduce the amount of memory space required for storing data and calculating parameters within the sample analysis device which might be particularly helpful for decreasing the size of a hand-held device.

By using a derivative of the measurement curve, when assuming an exponential characteristic, the offset of the measurement curve may easily be eliminated. Similarly, by assuming an exponential characteristic, the decay rate $\Gamma$ and/or the contrast b of the exponential function may be determined without using a fit, by forming the above-mentioned quotient of two subsequent derivatives of the measurement curve. Thus, the effort and the resources for performing a fit may even fully or partially be eliminated. Therewith, the costs of the evaluation device and/or of the sample analysis device may significantly be reduced. Further, the lifetime of a battery and/or another optional energy storage device of the sample analysis device may be significantly increased.

The assumption of an exponential characteristic and the use of a fit of an exponential function may also be extended, by using a "stretched" exponential function, as indicated by equation (4) below. Therein, the stretching parameter $\beta$ may be used as an additional parameter, which, in addition to or as an alternative to the other parameters a, b and $\Gamma$, may be dependent on the analyte concentration, such as the glucose concentration, and, in addition, may depend on one or more disturbance variables, such as Hct, relative humidity, temperature and other disturbance variables. Thus, the stretch factor $\beta$ may be used for correcting the analyte concentration, by using the methods disclosed herein.

Methods

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps. Likewise, one of the steps or a plurality of the steps or even all of the steps may be performed by using a data processing device such as a computer, preferably a microcomputer and/or an application-specific integrated circuit (ASIC).

Methods incorporating the inventive concept firstly can include methods of deriving at least one analyte concentration in a body fluid sample. Briefly, the methods include the following steps:

Step (a): recording a plurality of measurement values by monitoring a time development of at least one measurement value indicating a progress of a detection reaction of at least one test substance and a body fluid sample, and providing at least one measurement curve F(t) that contains the measurement values, where at least an evaluation part of the measurement curve has an exponential characteristic, where the measurement values contained in the measurement curve are acquired at differing points in time, and where the detection reaction is influenced by an analyte concentration c to be detected in the body fluid sample and at least one disturbance variable Y.

Step (b): deriving an end value of the measurement curve, where the end value forms a first variable $x_1$;

Step (c): deriving at least one fit parameter from the measurement curve by taking into account the exponential characteristic of at least the evaluation part of the measurement curve, where the fit parameter forms at least one second variable $x_2$; and Step (d): deriving the analyte concentration c by using at least one multivariate evaluation algorithm, the multivariate evaluation algorithm being adapted to combine the first variable $x_1$ and the second variable $x_2$.

Alternatively, the methods can include the following steps:

Step (a'): providing at least one measurement curve F(t), where the measurement curve contains a plurality of measurement values recorded by monitoring a time development of at least one measurement value indicating a progress of a detection reaction of at least one test substance and the body fluid sample, where the measurement values contained in the measurement curve are acquired at differing points in time, where the detection reaction is known to be influenced by an analyte concentration c to be detected in the body fluid sample and at least one disturbance variable Y;

Step (b'): deriving an end value of the measurement curve, where the end value forms a first variable $x_1$;

Step (c'): deriving at least one fit parameter from the measurement curve by assuming an exponential characteristic of at least an evaluation part of the measurement curve, where the fit parameter forms at least one second variable $x_2$; and Step (d'): deriving the analyte concentration c by using at least one multivariate evaluation algorithm, the multivariate evaluation algorithm being adapted to combine the first variable $x_1$ and the second variable $x_2$.

As noted above, the methods can include these steps, which may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

With respect to step (a), it is contemplated that any known electrochemical, optical or combination thereof may be used to obtain and thus record measurement values from a detection reaction between of at least one test substance and a body fluid sample. As such, exhaustive details on these known methods need not be provided herein.

As used herein, "measurement value" means a quantifiable measurement result $R_i$ recorded by an arbitrary measurement method based on at least one of a physical, chemical and biological measurement principle. The type of measurement values may strongly depend on the type of detection reaction, as will be explained in further detail below. Thus, by using the measurement methods described herein, at least one measurement value may be determined that is known to be influenced by a detection reaction of the test substance. This measurement value may be or may include at least one of an electrical measurement value and an optical measurement value, especially an optical measurement value.

For example, the test substance may be part of a test field or a test area of a test element, such as a test strip. The measurement value may be an optical characteristic of the test substance, specifically the test field, such as a color and/or a photometric measurement value such as a remission value, as known in the art. The measurement value may be determined by using at least one detector, such as at least one optical detector. The detector may include at least one light-sensitive element adapted to determine an intensity of light reflected by and/or emitted from the test substance, such as a test field of a test element comprising the test substance. The detector also may include one or more light sources for illuminating the test substance, such as for illuminating the test field. However, additionally or alternatively, other measurement principles for determining the measurement value are feasible.

As used herein, "recording" means acquiring at least one measurement value of a body fluid sample by, for example, applying at least one of a physical, chemical and/or biological measurement principle, particularly by employing an optical measurement principle. In this manner, the recording of the measurement value may be performed in form of a spot measurement (i.e., a measurement technique where the measurement value may be taken within a single small area, also denoted as spot) to acquire an integral value over an entire region and/or a representative value of the entire region where the measurement could be reasonably performed. In addition, the recording of the measurement value in the body fluid sample may be performed as an in vitro measurement, which means that the body fluid sample may be isolated from the body and, thus, separated from its common biological surroundings (i.e., the recording may be performed in an extra-corporal manner with respect to the body from which the sample may be taken). In some instances, generating the sample by isolating the body fluid from the related body may take place prior to the recording of the at least one measurement value. In other instances, generating the sample may be performed as a part of the method for analyzing the sample of the body fluid, whereby generating the sample may involve only a minor puncturing of the skin of the body, especially at a peripheral part of the body, such as the fingertip or the ear lobe.

As used herein, "measurement curve" or "F(t)" means an overall amount of data characterizing the time development or time sequence of the detection reaction. The measurement curve contains a plurality of measurement values as discussed above, recorded at different points in time. The measurement curve optionally and/or additionally may include the respective measurement times $t_i$ of the measurement values $R_i$, such as by containing data pairs $(R_i, t_i)$ and/or $(t_i, R_i(t_i))$. As will be outlined in further detail below, the original measurement curve may further be replaced by a first order or higher order derivative, which then forms a "new" measurement curve. In the following, both the option of using the original measurement curve and the option of using the new measurement curve are encompassed by "measurement curve."

As used herein, "monitoring" means acquiring and, optionally, storing a plurality of measurement values acquired at different points in time. Thus, monitoring simply may include acquiring electronic measurement values in conjunction with their respective times of measurement and/or acquisition. The monitoring may optionally include any type of a pre-processing, processing or evaluation of the measurement curve, such as a filtering and/or a smoothing.

As used herein, "analyzing" means determining at least one of a presence and a concentration of at least one constituent or component of the body fluid. In this manner, the analysis may be a qualitative and/or a quantitative analysis. In some instances, the analysis is a quantitative determination of the concentration of at least one component of the body fluid, also referred to as the analyte. The analyte, as outlined above, may be glucose, and the body fluid may be one of blood and/or interstitial fluid. However, other embodiments are feasible.

As used herein, "detection reaction" means an arbitrary type of chemical reaction of at least one test substance and the body fluid sample, where the detection reaction is adapted to generate analysis information. For example, the detection reaction can be a chemical reaction between at least one component of the test substance that is adapted to indicate the presence and/or the concentration of the at least one analyte in the body fluid sample. In this manner, the test substance may be a chemical compound and/or a chemical mixture adapted to react with the at least one analyte to be detected, particularly in a highly analyte-specific fashion. The detection reaction may be embodied such that the test substance reacts with the at least one analyte to be detected and, thereby, may fully or in part change by itself, may transform into another chemical species and/or may transform its surrounding in a detectable way, which may be measured, thereby deriving the plurality of measurement values and the measurement curve. The progress of the detection reaction may be indicated by at least one physical measurement value and/or a change in at least one physical measurement value, which may be used as the measurement value as outlined above. In some instances, the detection reaction is an optically detectable detection reaction, which may be optically observable, such as by using a reflection measurement and/or a transmission measurement. Other types of measurements are feasible.

As used herein, "test substance" means a chemical compound or substance or a mixture of two or more chemical compounds or substances adapted for performing the above-mentioned detection reaction, especially an analyte-specific detection reaction. In some instances, the test substance may include one or more enzymes adapted to react with the at least one analyte to be detected. Additionally, the test substance may include one or more auxiliary components, such as mediators and/or co-enzymes. For test substances that also may be used within the methods described herein, reference may be made to the test substances known in the art, as discussed in more detail elsewhere, such as the cNAD test substances. Further examples will be given in further detail below.

Generally, with regard to potential test substances that may be used are disclosed in Hoenes et al., supra.; see also, Int'l Patent Application Nos. WO 2010/094426 and WO 2010/094427. Specifically, reference may be made to the test substance therein that includes an enzyme and a stable co-enzyme stored in common, specifically using carbaNAD (cNAD) as a stable co-enzyme. However, additionally or alternatively, other types of test substances may be used.

As used herein, "disturbance value Y" means a variable other than the analyte concentration c, which characterizes at least one of a state of the sample of the body fluid and a condition of the detection reaction, having an impact on the plurality of measurement values and/or the measurement curve. In particular, the disturbance variable Y may include a parameter that may be able to influence the viscosity of the body fluid. Examples of disturbance values are: (1) a content of at least one component of the sample of the body fluid, such as a content of a particulate component (e.g., Hct); (2) a temperature of the body fluid sample; (3) a humidity of an ambient atmosphere surrounding the body fluid sample; (4) a parameter characterizing the quality of the test substance, such as a storage time of the test substance, the conditions under which the test substance may be stored (e.g., a possible exposition to temperature and/or humidity), including fluctuations of the temperature and/or the humidity, or a possible degradation of the test substance, the test chemistry, or a component thereof, such as an enzyme, owing to an elevated temperature, a high humidity, or a volatile material being included within the test chemistry or within the testing device. Additionally or alternatively, other disturbances of the detection reaction, especially an influence arising from a geometry of test strips that may be engaged in determining the analyte, such as a top dosing, a capillary channel or another geometry, are known and may be characterized by the at least one disturbance variable Y.

As used herein, "end value" means a value of the measurement curve at a point in time the detection reaction has essentially finished, such as by at least about 70%, by at least about 80%, or by at least about 90%. Thus, the end value may be an asymptotic value of the measurement curve F(t), such as for high measurement times, or an estimated asymptotic value for these high measurement times, such as a best guess for the asymptotic value. For example, the end value may be a best guess for $\lim_{t\to\infty} F(t)$, even though the measurement time typically may be limited for practical reasons. As an example for determining the end value, the slope or change in the measurement curve might be monitored or evaluated, and once the slope or change reaches a predetermined threshold, an end point of the detection reaction may be determined, and some or more of the measurement values acquired at or after this end point may be chosen as the end value and/or the end value may be derived by combining the measurement values, such as by forming a mean end value. Examples of algorithms for deriving the end value are disclosed in, for example, EP Patent No. 0 821 234, US Patent Application Publication No. 2002/0146835 or EP Patent Application Publication No. 1 413 883. As a further example for determining the end value, the exponential characteristic of at least the evaluation part of the measurement curve may be taken into account, from which it may be concluded that the measurement curve might approach the end value in the form of a plateau, which means that the end value may be derived from any part of the measurement curve, particularly from a part of the measurement curve that may be distant from the plateau. Additionally or alternatively, other types of algorithms may be used for deriving an end value of the measurement curve.

As used herein, "fit" means an algorithm in which at least one curve to be fitted is approximated by at least one model curve or fit function, thereby modeling the shape of the curve by choosing the model curve or fit function appropriately, such as by choosing one or more parameters of the model curve or fit function appropriately. As a result of the fit, one or more fit parameters may be derived which, when used in the model curve or fit function, lead to an optimum similarity of the fit function and the curve to be fitted. To determine the similarity, known algorithms may be used. For the purpose of fitting, a large number of algorithms are known in the art, such as the method of least squares regression or least squares fit, the method of trusted region or heuristic fitting methods. Consequently, "fit parameter" refers to one or more parameters derived by the above-mentioned fit.

As used herein, "deriving" may include any procedure configured for acquiring the end value of the measurement curve. Herein, a procedure that may determine the end value by using an actually recorded property of the measurement curve and deriving therefrom the desired value may be particularly preferred. Examples for the actually recorded property include a slope of the measurement curve that may be compared to at least one threshold value, or a part of the measurement curve which may even be distant from the plateau formed by the end value. Alternatively, it may be feasible to determine the end value by using a model adapted to provide the end value from any known parameters otherwise related to the body fluid sample.

With respect to step (b), the slope of the measurement curve may be compared to the at least one threshold value for determining the measurement curve has reached the end value. For example, the slope may be formed by a difference value between neighboring measurement values of the measurement curve, specifically when a constant acquisition rate or when a measurement rate is used for acquiring the measurement values. Thus, difference values of neighboring measurement values may be formed and may be compared to at least one threshold value, for determining if the end point of the reaction has been reached. Additional criteria might be added, such as a criterion indicating that at least two, at least three or at least a specific number of neighboring difference values are below or above the threshold value. For example, the threshold value may be a threshold value indicating that a change in the reflectance values per second is below about 3%, about 2% or even about 1%.

Alternatively or additionally one may derive of the end value of the measurement curve according to step (b), where the end value forms a first variable $x_1$. This example may be based on the exponential characteristic of at least the evaluation part of the measurement curve. Taking the exponential characteristic of at least the evaluation part into account, it may be concluded that the measurement curve might approach the end value after a certain period of time, where the end value may exhibit the form of a plateau. Every measurement curve may form a same plateau value independent from the at least one disturbance variable Y. Thus, it might be possible to derive the analyte concentration c independent from the at least one disturbance variable Y.

For example, the glucose concentration may be derived from a remission curve in an optical measurement, since all remission curves may form the same plateau value independent from the actual Hct or temperature. Moreover, the exponential characteristic may be employed to determine the plateau value by utilizing measurement values taken from a part of the measurement curve that may not necessarily bear any relation to the plateau. At least the evaluation part of the measurement curve may include an exponential shape and may allow deducting information about the end value from any part of at least the evaluation part of the measurement curve. Consequently, the end value may be derived from an earlier part of the measurement curve, where the earlier part may be a part of the measurement curve being distant from the plateau. As a result, the end value may be derived in step (b) as the at least one first variable $x_1$ from at least one measurement value taken from the measurement curve whereas the at least one second variable $x_2$ may be derived in step (c) from at least one fit parameter as derived from the measurement curve.

This feature may imply that it may not be necessary to acquire measurement values until the measurement curve may have reached a predefined threshold value. Accordingly, it may rather be feasible to derive the end value already from the earlier part of the measurement curve, especially from the same part of the measurement curve in which the decay constant $\Gamma$ or a quantity that may be related to the decay constant $\Gamma$ may be determined as the second variable $x_2$.

Without losing information, a lower number of actually recorded measurement values may, thus, be sufficient for determining the analyte concentration c. On the other hand, since the accuracy of the end value may increase when the plateau value may be derived at a later part of the measurement curve, an optimum time to terminate the recording of the measurement values may be found somewhere midway through the measurement curve. Irrespective of the actually chosen time to terminate the recording of the measurement values, a saving of resources, including but not limited to, measurement time, calculating efforts and/or memory space, which may be achieved by way of the methods described herein.

As indicated above, the evaluation part generally may be an arbitrary part of the measurement curve or even the full measurement curve. For example, the evaluation part of the measurement curve is a part of the measurement curve starting at a predetermined or definable starting point after a commencement of a measurement (i.e., after applying the sample to the test substance and/or after a start of the detection reaction). For example, the evaluation part of the measurement curve may be a remainder of the measurement curves starting after a definable starting time span after a commencement of the measurement. The starting time span generally may be a definable or predetermined time span such as, for example, a fixed time span of about 0.5 s to about 3.0 s, about 1.0 s to about 2.0, or about 1.5 s to about 1.7 s. By applying this predetermined time span, an initial phase of the measurement curve may be excluded from the evaluation, where the initial phase may include a wetting period during which the test substance is wetted by the sample.

Further examples relate to the multivariate evaluation algorithm. As indicated above, the multivariate evaluation algorithm may be or may include an arbitrary one-step or multi-step evaluation algorithm that transforms the at least one first variable $x_1$ and the at least one second variable $x_2$ into the analyte concentration c and, optionally, into additional information.

In some instances, the multivariate evaluation algorithm might include a linear matrix algorithm and/or a linear equation, having two or more coefficients, by which the at least one first variable $x_1$ and the at least one second variable $x_2$ are transformed into the analyte concentration c and, optionally, into additional information, such as into the at least one disturbance variable Y.

Additionally or alternatively, the multivariate evaluation algorithm may be or may include a non-linear equation system and/or a non-linear transformation matrix algorithm, again which, again, includes two or more coefficients. Further, two or more evaluation algorithms may be provided, such as two or more transformation algorithms and/or two or more transformation curves. One or more of these evaluation algorithms may be chosen out of the plurality of multivariate evaluation algorithms, such as according to appropriate boundary conditions. For example, a temperature of the environment may be measured independently, and an appropriate multivariate evaluation algorithm corresponding to the specific ambient temperature as measured may be chosen from a plurality of multivariate evaluation algorithms, thereby choosing an appropriate multivariate evaluation algorithm for the respective temperature of the sample of the body fluid.

The methods described herein may further imply the use of at least one decision tree. As used herein, "decision tree" means at least one decision branch that may allow selecting one out of at least two, particularly two, alternative functions based on an assessment whether a predetermined condition may be fulfilled or not. The decision branch itself may include an additional second-order decision branch that may allow performing one out of at least two, particularly two, further alternative functions depending on the assessment of a further predetermined condition.

In addition, the second-order decision branch may include at least one further higher-order decision branch. In general, the predetermined condition may assess an existence of a value, a non-existence of a value, or whether a definite value falls within at least one predetermined range or not. The decision branch may, thus, offer a decision between performing or not performing a specific function or performing the specific function under a specific parameter, with a specific parameter set, or within a specific parameter range. For example, only such glucose values may be submitted to a correction procedure for which such a correction may be required (e.g., outside the predetermined Hct range). Another example may refer to threshold values that may be applied for determining the glucose concentration in a sample, where the actual threshold values applied within this procedure may be selected according to a predetermined glucose concentration range.

Alternatively or in addition, a weighted average may be employed within the method for analyzing the body fluid sample and for taking into account the results out of at least two, especially a multitude of, procedures based on variations of the at least one disturbance variable Y to derive a value for the analyte concentration c of the analyte. Herein, the weighted average may include weights denoting probabilities for each specific value of the disturbance variable Y according to a forecast model that may reflect the probability distribution of each specific value of the disturbance variable Y. For example, a number of glucose concentrations may, thus, be obtained, each glucose concentration for a specific value of the Hct within a predetermined range, and the weighted average thereof may be derived, thereby acquiring a single value for the glucose concentration. As such, the weights may denote probabilities for each specific value of the Hct according to a forecast model that may reflect the probability distribution of each specific value of the Hct.

The multivariate evaluation algorithm generally may be determined in a preceding method step, such as by using a plurality of calibration measurements. In a simple measurement setup, a plurality of calibration samples may be provided, having well-defined and different analyte concentrations and/or having well-defined and different disturbance variables. In a simple case, the multivariate evaluation algorithm may include a multiplicity of coefficients, such as the coefficients of a transformation matrix, which may be determined by solving the equation system resulting from applying these coefficients to the measurement results $x_1$ and $x_2$ resulting from measurements using the calibration fluids. One of skill in the art will recognize a number of potential calibration setups. As used herein, "calibration measurement" means an arbitrary measurement acquired by using a calibration fluid and/or acquired under known conditions, such that at least the concentration and at least one disturbance variable are known. Thus, in case the disturbance variable refers to the calibration fluid, the disturbance variable may be known via the calibration fluid itself, such as by using a calibration fluid having a predetermined Hct. In case the target variable refers to the measurement conditions, such as a temperature and/or specific properties of the test substance used for the measurement, the disturbance variable may be known from the circumstances of the measurement. Thus, by using one or more calibration measurements, at least one multivariate evaluation algorithm may be determined and/or a set of multivariate evaluation algorithms may be determined, and, in some instances stored in a data storage for later use in the methods described herein.

With respect to step (c), at least one fit parameter can be derived from the measurement curve by assuming an exponential characteristic of at least one evaluation part of the measurement curve. In this manner, the whole measurement curve or a part of the measurement curve, such as a part of the measurement curve starting at a predetermined point in time or at a determinable point in time after body fluid sample application and/or after the start of the detection reaction, may be evaluated.

As used herein, "exponential characteristic" means a property of a curve indicating that the curve at least partially follows or resembles a function containing one or more exponential terms. It might be taken into account that, within the methods described herein, a plurality of actual measurement values are recorded by using a physical monitoring of the time development of at least one real measurement value, which may be used for indicating the progress of the detection reaction of the at least one test substance. However, it may not be possible to acquire actual measurement values that might be free from any error or defect. Consequently, "exponential characteristic" may mean a situation where the curve including the plurality of actual measurement values at least partially follows or at least partially resembles a function having one or more exponential terms, where not every single measurement value may be obliged to obey this condition. For example, whereas an accurate exponential decay curve always requires a strictly monotonically decreasing behavior of two successive values, a real measurement curve may still be considered to exhibit the necessary exponential characteristic of at least the evaluation part of the measurement curve, even though some of the actually recorded measurement values may not follow the strictly monotonically decreasing behavior.

In some instances, one or more of the following exponential functions or exponential terms may be used as fit functions:

$$F(t)=a+b\cdot\exp[-\Gamma t] \qquad (1)$$

$$F(t)=a+b\cdot\exp[-\Gamma t+c] \qquad (2)$$

$$F(t)=a+b\cdot\exp[-(\Gamma t)^\beta] \qquad (3)$$

$$F(t)=a+b\cdot\exp[(-\Gamma t)^\beta+c] \qquad (4),$$

where a, b, c, $\Gamma$ and $\beta$ are parameters that may be chosen, predetermined or fitted, which may be positive or negative and which may be real numbers.

In method step (c), the measurement curve itself and/or an arbitrary secondary measurement curve derived from the measurement curve may be used. Both options are possible and shall be included by the scope of the disclosure. Thus, the "raw" measurement curve may, before the fitting process is performed, be subject to one or more filtering algorithms. Additionally or alternatively, one or more derivatives may be formed, thereby generating a first order derivative of the measurement curve and/or a higher order derivative of the measurement curve. Therein, arbitrary means for generating the derivatives may be used. For example, in case the measurement curve contains a plurality of measurement values acquired at a constant acquisition rate, difference values between neighboring measurement values may be formed, and the sequence of difference values formed this way may be used as a derivative of the measurement curve. Subsequent, higher order derivatives may be formed accordingly.

In some instances, in step (c), a first order derivative F'(t) or a higher order derivative F"(t) of the measurement curve is formed before deriving the fit parameter. Thus, the first order derivative F'(t) or the higher order derivative F"(t) may be subject to the fit step (c), thereby deriving the at least one fit parameter.

Generally, without restricting other embodiments, the measurement values may be acquired at predetermined and/or determinable points in time, and/or the measurement values may be acquired at a predetermined or determinable time span after the acquisition of the previous measurement value. For example, the time intervals between the acquisition of neighboring measurement values may be predetermined or determinable. In some instances, the measurement values of the measurement curve are acquired equally spaced in time (i.e., at a constant acquisition rate). Thus, the measurement curve may be acquired at a constant measurement rate or measurement frequency of about 10 Hz to about 100 Hz. However, other embodiments of acquisition of the measurement curve are feasible.

As outlined above, by using a simplified algorithm for deriving the first order or higher order derivatives, the first order or higher order derivatives may be approximated by calculating differences between neighboring measurement values.

Alternatively, in step (c), a ratio of two subsequent derivatives $F''(t)$ and $F''^{+1}(t)$ of the measurement curve is formed, where the ratio forms the fit parameter or, in case a plurality of fit parameters is used, at least one of the fit parameters. Again, the derivatives $F''(t)$ and $F''^{+1}(t)$ may be formed by using the above-mentioned approximation by using difference values of neighboring measurement values or values of the preceding derivative.

As used herein, "formation of a ratio of two subsequent derivatives $F''(t)$ and $F''^{+1}(t)$ of the measurement curve" means a quotient of function values the two subsequent derivatives $F''(t)$ and $F''^{+1}(t)$ at one or more specific points in time. Additionally or alternatively, a quotient of function values of the two subsequent derivatives may be generated over a specific time span or over a plurality of points in time. For example, an average value of a quotient of the function values of the two subsequent derivatives may be formed over a predetermined time span.

Additionally or alternatively to the option of using the "raw" measurement curve and/or a first order or higher order derivative thereof, an integral may be formed over the measurement curve. Thus, in step (c), an integral may be formed over the measurement curve $F(t)$ or a first order or higher order derivative of $F(t)$, the integral forming the fit parameter. As outlined elsewhere, the assumption of an exponential characteristic of the measurement curve may lead to the fact that the integration results in one or more highly useful fit parameters.

The process of forming an integral, also referred to as an integration, may include an arbitrary integration algorithm known to one of skill in the art. Since the measurement curve or a first order or higher order derivative of the measurement curve include discrete values such as the measurement values, the process of forming the integral may include a formation of a sum over all measurement values of the measurement curve or over a predefined group of measurement values of the measurement curve, as will be outlined in further detail below. Thus, the formation of the integral generally may imply the formation of a Riemann sum or a Riemann integral. Additionally or alternatively, however, other types of algorithms adapted for forming an integral may be used.

With respect to step (d), at least one multivariate evaluation algorithm can be used for deriving the analyte concentration c from at least two variables (i.e., the first variable $x_1$ (end value) and the second variable $x_2$ (fit parameter). One or more first variables and one or more second variables may be used.

As used herein, "multivariate evaluation algorithm" means a rule or set of rules for directly or indirectly deriving the analyte concentration c from the at least one first variable and the at least one second variable. The evaluation algorithm may include an arbitrary mathematical algorithm or arbitrary combination of algorithms for deriving the analyte concentration from the first variable and the second variable. Thus, the multivariate evaluation algorithm may be or may include a one-step algorithm in which the first variable and the second variable are used as input variables for one and the same algorithm, such as by using one and the same equation having the first variable and the second variable as input variables, thereby deriving the analyte concentration. Alternatively, the multivariate evaluation algorithm may be or may include multiple steps, where step-by-step, two or more algorithms are successively applied, thereby finally deriving the analyte concentration. In this manner, the first variable $x_1$ and the second variable $x_2$ may be used as variables for different steps or for the same step of the multi-step evaluation algorithm.

For example, the at least one fit parameter and the at least one end value may be used as input variables for one equation or one algorithm, thereby deriving the analyte concentration c in one step. Alternatively, the end value may be used for deriving an estimate value or rough value of the analyte concentration, which is subsequently corrected by applying a correction algorithm to the estimate value or rough value, where the correction algorithm includes the at least one fit parameter, and where the correction is performed in accordance with the at least one fit parameter.

The method as disclosed above may be modified or may be further improved in various ways. For example, the assumption of an exponential characteristic, which may lead to an appropriate fit function, may contain an exponential function selected from the group consisting of:

$$F(t)=a+b*\exp[-\Gamma*t],$$

where t is the time, a is an offset, b is a contrast, and $\Gamma$ is a decay constant;

$$F(t)=a+b*\exp[-(\Gamma*t)^\beta],$$

where t is the time, a is an offset, b is a contrast, $\Gamma$ is a decay constant, and $\beta$ is a stretching parameter.

In these functions, a, b, $\Gamma$ and t may be real numbers. By assuming one or more of these exponential characteristics, an appropriate fit function, such as one or more of the above-mentioned functions, may be chosen in method step (c).

The second variable $x_2$ may be selected from the decay constant $\Gamma$ or from a quantity related to the decay constant $\Gamma$. As such, the quantity may exhibit any relationship with the decay constant $\Gamma$, whereby a relationship where the quantity may be proportional to the decay constant $\Gamma$ or proportional to the inverse $1/\Gamma$ of the decay constant. However, other kinds of relationships that may be adapted to the particular circumstances can be employed. In some instances, a particularly significant data reduction may be achieved since the overall amount of data of the measurement curve may be reduced to the one fit parameter either being the decay constant $\Gamma$ or the quantity in relationship with the decay constant $\Gamma$. In other words, by taking into account the exponential characteristic of at least the evaluation part of the measurement curve, the decay rate $\Gamma$ and/or the quantity in relationship with the decay constant $\Gamma$ may be determined without applying a fit procedure, by simply taking two measurement values from the evaluation part of the measurement curve from which the fit parameter may be derived. Such an appreciable simplification of acquiring the fit parameter may primarily be considered as a consequence of the exponential characteristic of at least the evaluation part of the measurement curve.

In method step (d) and the above-mentioned multivariate evaluation algorithms, by using the at least one first variable $x_1$ and the at least one second variable $x_2$ and by using the above-mentioned multivariate evaluation algorithm, besides the at least one analyte concentration c, one or more further types of information may be generated. The multivariate evaluation algorithm may be an arbitrary algorithm or combination of algorithms by which, in addition to the analyte concentration c, additional information, such as the at least one disturbance variable, may be generated. Thus, generally, in step (d), further, the at least one disturbance variable Y may be determined.

For example, the multivariate evaluation algorithm may be or may include a matrix algorithm that transforms a first vector, including the at least one first variable $x_1$ and the at least one second variable $x_2$ into a result vector by using a linear, quadratic or higher order matrix transformation, where the result vector includes the analyte concentration c and at least one additional information, where the at least one additional information can be the at least one disturbance variable Y such as the at least one Hct and/or the temperature of the body fluid sample.

In this manner, the at least one multivariate evaluation algorithm may include a step of transforming the vector ($x_1$, $x_2$) by using a transformation matrix having coefficients $c_{ij}$, which may be determined by an arbitrary calibration algorithm. By multiplying the vector ($x_1$, $x_2$) with this matrix, a result vector (c, Y) might be generated. Other examples are feasible.

Computer Programs

Computer programs also are disclosed that incorporate the inventive concept. Such computer programs can include computer-executable instructions for performing one or more of the methods as disclosed herein when the program is executed on a computer or computer network. In connection with the methods, one, more than one, or even all of method steps a) to d) may be executed by using the computer program.

Specifically, the computer program may be stored on a computer-readable data carrier.

Computer program products with program code means also are disclosed that incorporate the inventive concept. Such products can be stored on a computer-readable data carrier to perform the methods disclosed herein when executed on a computer or computer network. As used herein, "computer program product" means the program as a tradable product. The product may generally exist in an arbitrary format, such as in a paper format, or on a computer-readable data carrier. Specifically, the computer program product may be distributed over a data network.

Data carriers having a data structure stored thereon also are disclosed that incorporate the inventive concept. The structures, which, after loading into a computer or computer network, such as into a working memory or main memory of the computer or computer network, may execute the methods disclosed herein.

Modulated data signals containing instructions readable by a computer system or computer network also are disclosed that incorporate the inventive concept. The data signals can perform the methods as disclosed herein.

With respect to such computer-implemented aspects of the disclosure, one or more of the method steps or even all of the method steps of the methods disclosed herein may be performed by using a computer or computer network. Thus, generally, any of the method steps including provision and/or manipulation of data may be performed by using a computer or a computer network. Generally, these method steps may include any of the method steps, typically except for method steps requiring manual work, such as providing the samples and/or certain aspects of performing the actual measurements.

These aspects further include:

A computer or computer network including at least one processor, where the processor is adapted to perform at least one of the methods disclosed herein;

A computer loadable data structure adapted to perform at least one of the methods disclosed herein while the data structure is being executed on a computer;

A computer program adapted to perform at least one of the disclosed herein while the program is being executed on a computer;

A computer program including program means for performing at least one of the methods described herein while the computer program is being executed on a computer or on a computer network;

A computer program including program means as described above, where the program means are stored on a storage medium readable to a computer;

A storage medium, where a data structure is stored on the storage medium and where the data structure is adapted to perform at least one of the methods disclosed herein after having been loaded into a main and/or working storage of a computer or of a computer network; and A computer program product having program code means, where the program code means can be stored or are stored on a storage medium, for performing at least one of the methods disclosed herein, if the program code means are executed on a computer or on a computer network.

Devices and Systems

Devices incorporating the inventive concept can include evaluation devices for analyzing at least one body fluid sample. In view of the methods described herein, the evaluation devices may be adapted for evaluating a measurement curve for the purpose of analyzing a body fluid sample.

The evaluation devices include at least one evaluation unit, where the evaluation unit is adapted to perform at least one method as described herein. Thus, the evaluation unit may include one or more data processing devices, such as one or more computers and/or application-specific integrated circuits (ASICs), such as at least one microcomputer. The at least one data processing device may include one or more software components adapted to run on the data processing device, the software components being adapted to perform a method as described herein, fully or partially (e.g., except for specific measurement steps that might be involved in recording the measurement values and which might be performed by one or more measurement devices connected to the processor). The measurement values, in the latter case, may be provided to the evaluation unit, as a part of the recording step. The evaluation unit, which may be or which may include one or more components, may be adapted to perform a software algorithm implementing a method as described herein.

In addition to evaluation devices, sample analysis devices are provided for characterizing a sample of a body fluid. As used herein, "characterizing" means a process of determining one or more properties of the body fluid sample. Specifically, as will be disclosed in further detail below, "characterizing" means that a concentration of at least one analyte in the body fluid sample may be determined. Additionally, one or more items of information regarding the body fluid sample may be generated, such as an information on the at least one disturbance variable Y.

The sample analysis devices include at least one measuring unit for measuring a detection reaction of at least one test substance and at least one body fluid sample. The detection reaction is known to be influenced by a set of disturbance variables, each disturbance variable characterizing at least one of a state of the body fluid sample and a condition of the detection reaction. The measuring unit further is adapted for monitoring a time development of at least one measurement value indicating a progress of the detection reaction, thereby recording a measurement curve F(t) containing a plurality of the measurement values acquired at different points in time.

The at least one measuring unit, as outlined above, may include one or more detectors for measuring the plurality of measurement values, which, in the following, will be denoted by $R_i$, the plurality of measurement values forming the measurement curve F(t) and/or a part of the measurement curve. The at least one detector may be or may comprise an arbitrary element for determining the at least one measurement value, such as an optical detector and/or an electrical detector. For example, an optical detector may be provided, having at least one light-sensitive element, such as a photodiode and/or a photocell, for measuring light reflected by the test substance, such as by a test field of a test element. Such test fields typically include the test substance, and/or by measuring light transmitted by the test substance.

The at least one detector may further include one or more light sources for illuminating the test substance, such as one or more of a light-emitting diode, a laser diode or a light bulb. In this case, the measuring unit may be adapted to acquire the measurement values generated by the detector, which may be provided in an arbitrary form, such as in the form of electrical signals and/or in the form of analog and/or digital signals. The measuring unit may further be adapted for storing these measurement values and/or for transferring these measurement values to another unit of the sample analysis devices, such as to a display or to an evaluation device as disclosed elsewhere herein.

The sample analysis devices also include at least one evaluation device as described herein. As above, the evaluation device may be or may include at least one data processing device, such as at least one computer or computer network, including a microcomputer integrated into the sample analysis device, and/or may be or may include a computer connected to the measuring unit by at least one interface and/or at least one data connection.

The test substance may be part of a test element. The test element may include one or more test fields having the at least one test substance, such as one or more test fields applied to a surface of a carrier element of the test element. For example, the test element may be or may include one or more of a test strip, a test tape, a test disc or any other type of test element known in the art. The test element generally may contain the at least one test substance adapted to perform the detection reaction. Consequently, the sample analysis devices are adapted such that the body fluid sample can be applied to the test element. Thus, the sample analysis devices may include one or more receptacles for receiving the at least one test element, where the test element and/or the sample analysis devices include one or more application positions and/or application mechanisms in which the body fluid sample may be applied to the at least one test substance.

EXAMPLES

The inventive concept will be more fully understood upon consideration of the following non-limiting examples, which are offered for purposes of illustration, not limitation.

FIG. 1 shows an exemplary sample analysis device 110 in a cross-sectional view and in a schematic setup. The sample analysis device may be a hand-held device 112 and may include a casing 114 with one or more human machine-interfaces, such as one or more displays 116 and/or one or more controls 118, such as one or more push buttons and/or other types of controls. The sample analysis device 110 also may include one or more data interfaces 120, such as one or more infrared interfaces and/or wire-based interfaces and/or wireless interfaces. The sample analysis device 110 further may include an energy storage, such as a battery (not shown).

The sample analysis device 110 is adapted for analyzing a body fluid sample applied to a test element 122. In FIG. 1, the test element 122 may be a strip-shaped test element (i.e., a test strip) having one or more test fields 124 to which the sample may directly or indirectly be applied. The test field 124 includes a test substance 126 adapted to perform a detection reaction in the presence of an analyte, where the detection reaction is adapted to change at least one physical and/or chemical property of the test substance 126, which may be observed by, for example, an optical characteristic. In FIG. 1, the test substance 126 is adapted to change at least one optical property, such as a reflectance and/or a color.

For monitoring the progress of the detection reaction, the sample analysis device 110 includes a measuring unit 128, which may include a detector 130 having at least one light source 132 for illuminating the test field 124, and further may include at least one light-sensitive element 134 for detecting light reflected by the test field 124, particularly in an undirected manner, such as scattered light and/or diffused light. Thus, the detector 130 may be set up to perform a remission measurement on the test field 124. However, additionally or alternatively, other types of measurements for recording measurement curves containing a plurality of measurement values may be used.

The sample analysis device 110 also includes an evaluation device 136, which also may function as a control device of the sample analysis device 110 and which may be connected to the display 116, the controls 118, the measuring unit 128 and the data interface 120, in a unidirectional and/or bidirectional manner. The evaluation device 136 may thus be adapted to control the overall functionality of the sample analysis device 110.

The evaluation device 136 includes at least one evaluation unit 138, which may be or which may include a data processing device, such as a computer, particularly a microcomputer. The evaluation unit 138 is adapted to perform a method as described herein. For this purpose, the evaluation unit 138 may be adapted to initiate the acquisition of data by the measuring unit 128, such as the recording of the measurement curve, and/or may be adapted for performing the evaluation algorithm as described herein.

It shall be noted that the sample analysis device 110 as depicted in FIG. 1 is just one of many examples of analysis devices 110 adapted for performing a method as described herein.

With respect to the test element 122, it includes at least one test field 124 having at least one test substance 126. For the purpose of the measurements and evaluation of these measurements as given below, two different types of test substance 126 were used.

One test substance was a "PQQ chemistry," which is disclosed in EP Patent Application Publication No. 0 354 441. This test substance includes a PQQ-dependent dehydrogenase and a direct electron acceptor, which is an aromatic nitroso compound or an oxim. The PQQ chemistry also includes an optical indicator substance (i.e., a dye). For example, a hetero-polyblue indicator may be used, as disclosed in EP Patent Application Publication No. 0 431 456.

The other test substance was a "cNAD chemistry," which is disclosed in Int'l Patent Application Publication Nos. WO 2007/012494, WO 2009/103540, WO 2011/012269, WO 2011/012270 and WO 2011/012271. In particular, Int'l Patent Application Publication No. WO 2007/012494 generally discloses cNAD derivatives; WO 2009/103540 discloses a stabilized enzyme/coenzyme complex; and WO 2011/012269, WO 2011/012270 and WO 2011/012271 disclose the synthesis of cNAD and cNAD-derivatives and intermediate products or precursors.

By using the PQQ chemistry and the cNAD chemistry, the following measurements were performed.

In a first set of measurements, depicted in FIGS. 2A to 5B, it was shown that for both the PQQ chemistry and the cNAD chemistry measurement curves of a remission characteristic may be recorded by, for example, using the setup of FIG. 1, which may very well be described by assuming an exponential characteristic of at least an evaluation part of the measurement curves. In addition to an end value of the measurement curves, at least one fit parameter may be derived from the measurement curve and/or one or more derivatives of the measurement curve. Therein, the term fit parameter may be a parameter derived from the measurement curve itself and/or a first order or higher order derivative of the measurement curve.

Thus, in typical blood glucose measurements, the end value is used for determining the glucose concentration in blood. The determination of the end value, which also may be used herein and which will not be explained in further detail herein may be performed according to, for example, EP Patent No. 0 821 234, US Patent Application Publication No. 2002/0146835 or EP Patent Application Publication No. 1 413 883. Thus, as an example, the slope of the measurement curves may be compared to one or more threshold values and, as soon as the slope fulfills a predetermined condition, such as when the slope is below a given percentage per second (such as the remission curve having a negative slope of less than about 2% per second), the end value of the measurement curve may be determined.

In FIG. 2A, measurement curves for two different blood glucose concentrations (462 mg/dl and 59 mg/dl) are shown. Therein, the relative remission R, as detected by detector 130, given in percent, is depicted as a function of measurement time t, given in seconds after sample application to the test element 122.

By using the end value algorithm, a first variable $x_1$ may be derived from the measurement curves in FIG. 2A, which in this measurement may be determined to be about 73% for the lower measurement curve (concentration c=462 mg/dl) and about 100% for the upper measurement curve (concentration c=59 mg/dl).

Thus, in traditional measurements, one data value of the remission curves is used for determining the glucose concentration.

By using only the first variable $x_1$ (i.e., the end value), the measurement results are highly susceptible to disturbances by one or more disturbance variables inherent to the sample and/or inherent to the measurement setup or the conditions of the measurement. Thus, as will be explained in further detail below, the Hct may have a significant impact on the glucose concentration as determined by the end value.

The methods as described herein therefore derive at least one further variable (second variable $x_2$) by taking into account an exponential characteristic of the measurement curve. For this purpose, the measurement curves themselves may be evaluated and/or one or more first order or higher order derivatives of the measurement curves, which, by themselves, form new measurement curves, may be used.

As an example, one or more of the fit functions (1) to (4) may be used, where in the following measurements shown in FIGS. 2A to 5B, fit function (1) is used:

$$F(t)=a+b\cdot\exp[-\Gamma t].$$

By using this fit function, the information of the measurement curve (i.e., of the remission kinetics) may be reduced to three parameters: (1) the base line or offset a, (2) the contrast or amplitude b, and (3) the decay rate F. As will be shown, specifically the contrast b and the decay rate $\Gamma$ strongly depend on one or more disturbance variables, such as the Hct, the temperature, or the relative humidity. Thus, by determining one or more of these fit parameters and using one or more of these fit parameters as a second variable $x_2$, in conjunction with an appropriate multivariate evaluation algorithm, a correction algorithm adapted for correcting the "raw glucose concentration" for the actual set of disturbance variables may be provided.

For performing an exponential fit, surprisingly, it turned out that a methodological advantage may be gained by using a first or higher order derivative of the measurement curves rather than the measurement curves themselves. In FIG. 2B, first order derivatives of the measurement curves shown in FIG. 2A are shown.

For generating the first order derivative or generating higher order derivatives, it turned out that these derivatives, in case the measurement curves are generated by using measurement values acquired at a constant acquisition frequency, may easily be derived by forming difference values of neighboring measurement values. Thus, in FIG. 2B, difference values of neighboring measurement values are depicted as $R(t_1)-R(t_2)$. These differences are depicted as a function of the measurement time after sample acquisition. This type of analysis using first order or higher order derivatives of the measurement curve simplifies analysis because the offset should generally be eliminated, as depicted in FIG. 2B.

It shall be noted, however, as already outlined in detail above, that other options are feasible. Thus, the measurement values do not necessarily have to be acquired at a constant acquisition frequency. In some instances, however, the acquisition times and/or the time spans or time distances between neighboring measurement values are known to derive the first order or higher order derivatives by dividing differences of neighboring measurement values by the respective time span between the measurement values, as known to one of skill in the art. Using a constant acquisition frequency, however, allows for neglecting the aspect of the measurement time, since in this case, the acquisition frequency simply provides a constant factor to all difference values between neighboring measurement values. A significant simplification of the procedure therefore may be achieved, which may lead to an increased speed of the algorithm and to a lowering of resources required for performing the algorithm.

It turned out that the curves depicted in FIG. 2B may well be described by using an exponential characteristic, at least in an evaluation part of the measurement curve, which starts at 1.7 s after sample application. In the following, as an evaluation part of the measurement curves, a time window of about 1.7 s to about 7 s after sample application to the test element 122 was used. The evaluation part of the measurement curve, however, may be optimized and may be adapted later on. Thus, the evaluation part may be adapted in case a different type of test substance 126 is used and may easily be determined for the measurement curves by appropriate tests.

In FIGS. 3A and 3B, an exponential fit to the first order derivatives depicted in FIG. 2B is shown. FIG. 3A shows the first order derivative measurement curve for c=462 mg/dl, and FIG. 3B shows the fit for c=59 mg/dl, where the solid lines depict the fit curves.

By using these fit functions, a contrast b of approximately 0.016 for c=462 mg/dl and of b approximately 0.003 for 59 mg/dl was derived (both values given in percent), and a decay rate Γ of approximately 0.93 1/s for 462 mg/dl and of approximately 0.22 1/s for 59 mg/dl.

As it turned out, these fit parameters may strongly depend on one or more disturbance values, such as the temperature, the relative humidity, or the Hct of the blood. This dependency is shown in FIGS. 4A and 4B. Specifically, FIG. 4A shows the influence of Hct on the contrast b, and FIG. 4B shows the influence of Hct on the decay rate F. In FIG. 4A, the contrast b (given in percent) is depicted as a function of the concentration c, and in FIG. 4B, the decay rate Γ, given in 1/s, is depicted as a function of the analyte concentration c.

The measurement curves clearly show that, for one and the same glucose concentration c, the fit parameters b and Γ significantly decrease with an increase in Hct. These measurements were performed by using a cNAD chemistry. Similar measurements may be performed for the influence of the relative humidity and show a similar dependency. In contrast with these results, it could be demonstrated that, at least under ambient conditions, the temperature may only slightly be able to influence these measurements as a kind of disturbance variable. However, other circumstances may be feasible. Consequently, the methods as described herein may particularly be suited to be employed within a procedure of determining the glucose concentration c under the influence of the Hct and/or humidity.

In FIGS. 5A and 5B, fit curves for PQQ chemistry, in analogy to the fit curves of FIGS. 3A and 3B, are shown, for concentrations of 462 mg/dl (FIG. 5A) and 59 mg/dl (FIG. 5B), which clearly demonstrates that the assumption of an exponential characteristic is valid for various types of test substances.

The measurements depicted in FIGS. 2A to 5B therefore demonstrate that, at least in an evaluation region from 1.7 s after wetting to 7 s after wetting, the remission curves or their first order or higher order derivatives may well be described by assuming an exponential characteristic. In addition to an end value, one or more further variables $x_2$ may be generated by generating appropriate fit parameters. These fit parameters and second variables depend on one or more disturbance variables, such as the Hct. Thus, by using the end value as a first variable $x_1$ and the at least one fit parameter as at least one second input variable $x_2$, a corrected value for the glucose concentration may be generated, by using an appropriate multivariate algorithm.

By the measurements shown in FIGS. 2A to 5B, two different concepts of this disclosure were demonstrated: firstly, the option of evaluating the measurement curve itself, assuming an exponential characteristic of the measurement curve and, secondly, the option of using a first order or higher order derivative of the measurement curve as a "new measurement curve" for deriving the second variable $x_2$. In the following, two further concepts will be demonstrated, which may be used in addition or as an alternative.

Figure 6:
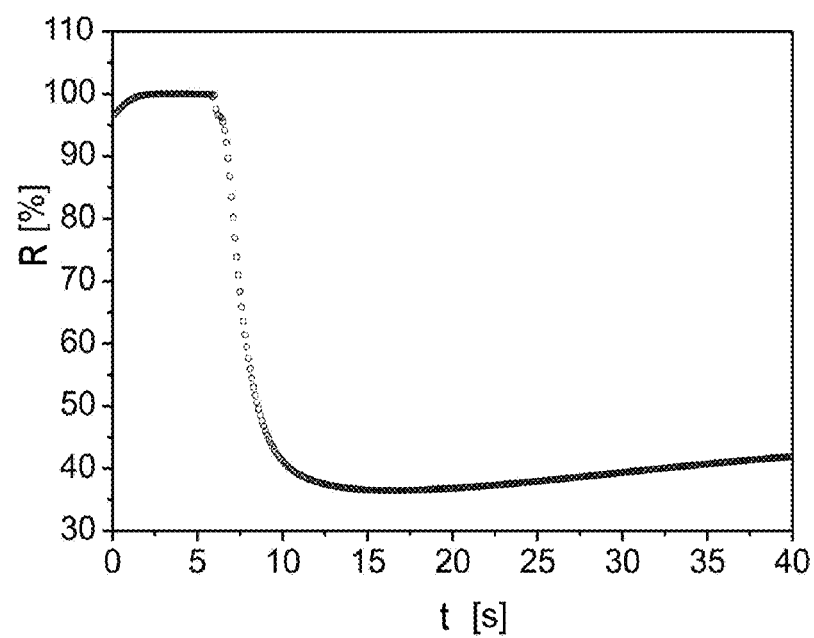
FIG. 6 shows a remission curve used for subsequent evaluation in FIGS. 7A to 8B.

Thus, in FIGS. 6 to 8B, a third concept is demonstrated, which is based on the use of two derivatives of higher order of the measurement curve as "new measurement curves." For example, in FIG. 6, a remission characteristic R is depicted as a function of time after application of the body fluid sample. This remission curve was derived by using the PQQ chemistry.

By assuming an exponential characteristic, such as the exponential characteristic (1) given above, it turns out that the decay rate Γ of the exponential characteristic may be derived experimentally in a simplified manner. Thus, the derivative of $n^{th}$ order may be divided by the derivative of $(n-1)^{th}$ order, for n being an integer and n≥1. In case the base line is neglected (a=0), as an example, the first order derivative is:

$$F'(t)=b \cdot \exp(-\Gamma t).$$

Similarly, the second order derivative may be calculated as:

$$F''(t)=-b \cdot \Gamma \cdot \exp(-\Gamma t).$$

By using these equations, the quotient of the second order derivative and the first order derivative is calculated as:

$$F''(t)/F'(t)=-b \cdot \Gamma \cdot \exp(-\Gamma t)/b \cdot \exp(-\Gamma t)=-\Gamma.$$

Figure 7:
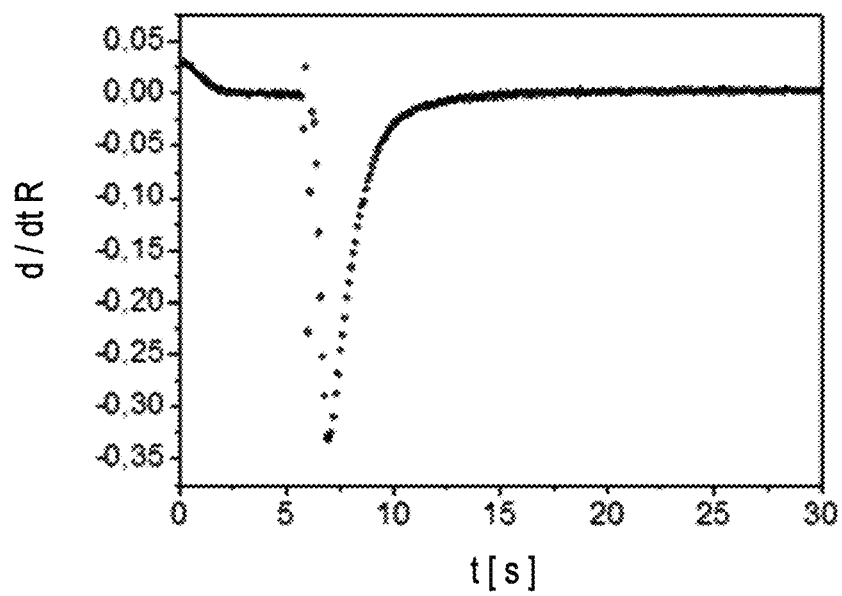
FIG. 7A shows a first order derivative of the measurement curve in FIG. 6.
FIG. 7B shows a second order derivative of the measurement curve of FIG. 6.
Figure 7:
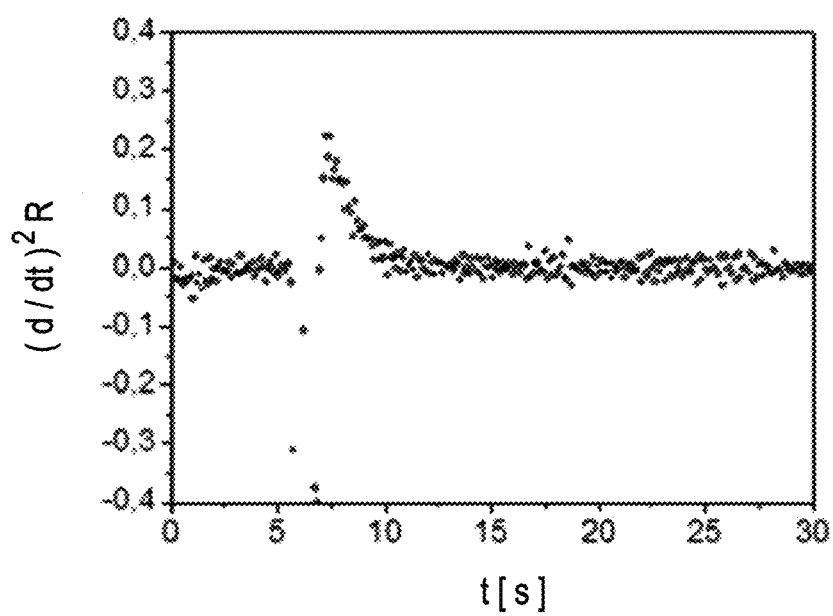

This idea allows for a simple and efficient evaluation of the measurement curves, as will be shown in FIGS. 7A to 8B. For example, FIG. 7A shows the first order derivative of the measurement curve, which may easily be generated by forming difference values between neighboring values, as disclosed with respect to FIG. 2B above. Similarly, FIG. 7B shows the second order derivative of the measurement curve, derived by forming difference values between neighboring measurement values of the first order measurement curve of FIG. 7A. Higher order derivatives may be formed in a similar way.

Figure 8:
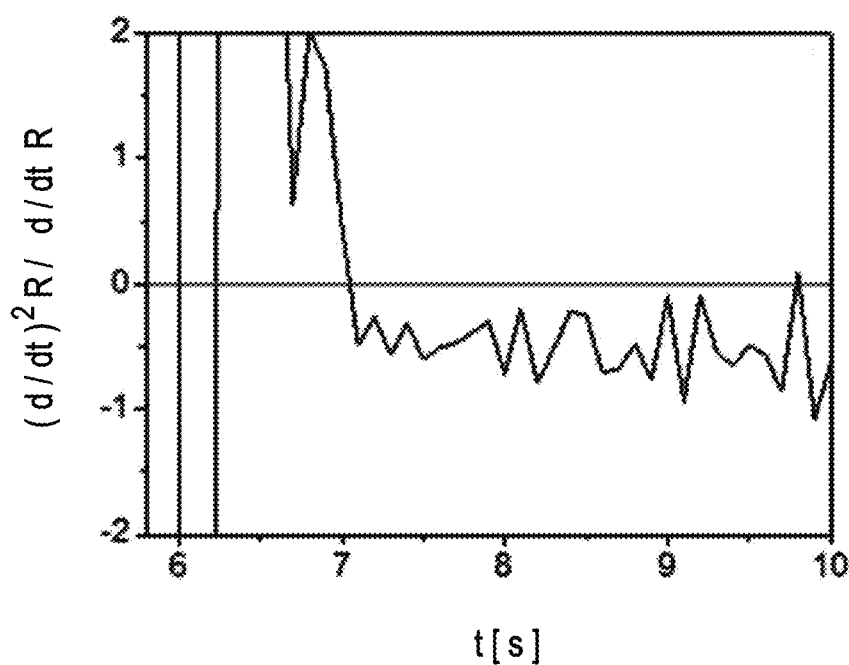
FIG. 8A shows a quotient of the second order derivative and the first order derivative of FIGS. 7B and 7A.
FIG. 8B shows an exponential fit to the first order derivative in FIG. 7A.
Figure 8:
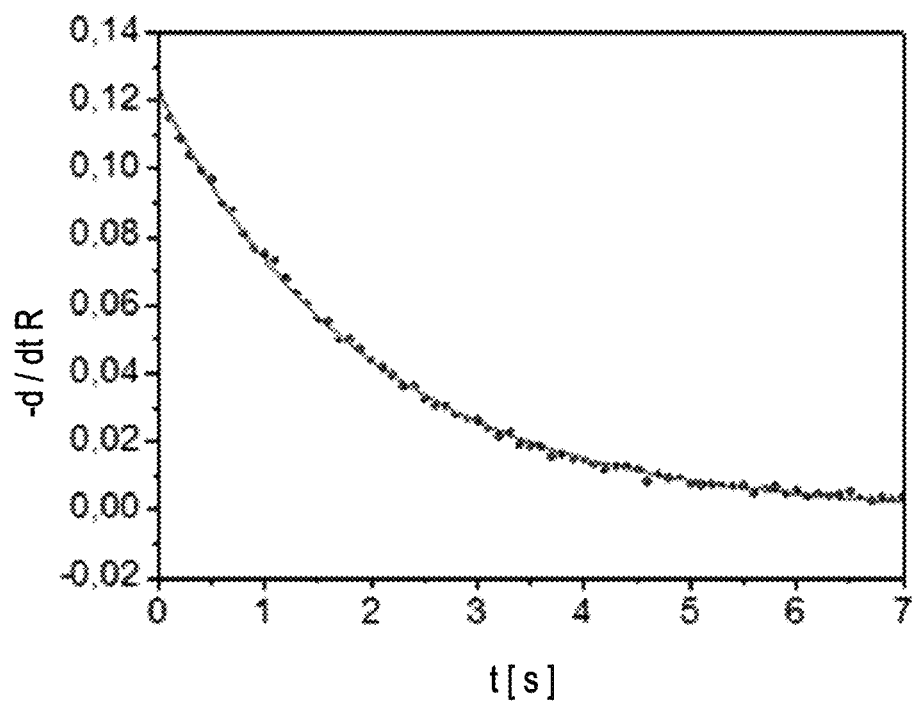

In FIG. 8A, a quotient of the measurement values of the measurement curves in FIGS. 7A and 7B is given as function of time t. As can be seen, the quotient, within uncertainty of measurement, starting at approximately 7 s, assumes a more or less constant value. For the first 20 values starting at 7.5 s, a mean value of r=0.494 1/s for concentrations of c=136 mg/dl may be derived, and a value r=0.82441 1/s for glucose concentrations of 446 mg/dl. In FIG. 8B, for reasons of comparison, an exponential fit to the first order derivative is depicted for concentrations of 136 mg/dl, which leads to a fit parameter Γ of 0.507 1/s. The comparison of the measurements in FIGS. 8B and 8A clearly demonstrates that the fitting of an exponential curve may be replaced by a fit by using the quotient of two derivatives of the measurement curve of a different order. By both methods, the fit parameter Γ may be derived which, by itself or in conjunction with other fit parameters, may be used as the at least one second variable, such as by using the multivariate evaluation algorithm given above. Thus, the quotient method as depicted in FIGS. 7A to 8B, specifically when generating derivatives by using the difference method disclosed above, leads to a simple and, still, effective fitting algorithm for deriving the fit parameter Γ in a simple and effective way. Thereby, resources and time may be saved.

In addition to this third option (i.e., quotient method) as explained in conjunction with FIGS. 6 to 8B, other options for simplified generation of fit parameters exist. As an example of a fourth option, an integral may be used. For example, when the base line a is neglected (a=0) or in case the first order or a higher order derivative of the measurement curve is used as a new measurement curve, the measurement curve may, as outlined above, be described by:

$$F(t)=b \cdot \exp(\Gamma \cdot t),$$

where $\Gamma$ denotes the decay rate and b denotes the contrast. By integrating this function from 0 to ∞, the following result may be derived:

$$\int_0^\infty b \cdot \exp(-\Gamma \cdot t) = b/\Gamma.$$

Thus, by using an integral and integrating over the measurement curve or a first order or higher order derivative of the measurement curve as a "new measurement curve," a simple and effective way of generating b/$\Gamma$ as a fit parameter and as a variable $x_2$ may be realized.

Similarly to the simplified method of forming a first order or higher order derivative of the measurement curve by using the difference method forming difference values of neighboring measurement values as disclosed above, the formation of an integral may be simplified, too. Thus, the integral may be calculated as:

$$\int_0^\infty b \cdot \exp(-\Gamma \cdot t) \approx \Sigma R_i \cdot \Delta t.$$

This approximation is referred to as the Riemann integral or Riemann sum. Therein, the sum over the measurement values $R_i$ of the measurement curve or of the first order or higher order derivative of the measurement curve is formed over the evaluation part of the measurement curve. When assuming a constant measurement frequency, the time $\Delta t$ between the measurement values is constant. In this case, the above-mentioned formula may be simplified to:

$$b/\Gamma \approx \Delta t \cdot \Sigma R_i,$$

where $R_i$ are the measurement values of the measurement curve or a first order or higher order measurement curve, and where the sum is formed over the evaluation part of the measurement curve. For example, for the measurements shown in FIGS. 2A to 3B, the sum may be formed from 1.7 s after wetting to 8.7 s after wetting. Thus, in a simple and efficient way, the fit parameter b/$\Gamma$ or similar fit parameters may be generated by using a simple integration process.

By using this integration, for a glucose concentration of 446 mg/dl, a value b/$\Gamma$=0.3164 was derived. This value, within experimental uncertainty, corresponds to the value b/$\Gamma$=0.2867, which was derived by fitting an exponential function to the first order derivative. For a glucose concentration of 136 mg/dl, by using the integration method, a value b/$\Gamma$ of 0.2353 was derived. By using an exponential fit, a value b/$\Gamma$=0.244 was derived.

As outlined above, the fit parameter b/$\Gamma$ may be used as the at least one second variable $x_2$ or as one of a plurality of second variables $x_2$ and, in combination with the first variable $x_1$, may be used in a multivariate evaluation algorithm, such as the algorithm disclosed above, for generating a corrected value of the glucose concentration, taking into account one or more disturbance variables, such as the Hct.

In addition to the one or more fit parameters derived by assuming an exponential characteristic, one or more of the disturbance variables that are known to have an impact on the evaluation of the glucose concentration or, generally, the analyte concentration, may be measured or detected independently. Thus, for example, the temperature and/or the relative humidity may be measured independently. In this case, for example, a plurality of multivariate evaluation algorithms may be provided, such as a set of evaluation algorithms, for the respective disturbance variables. For example, one specific evaluation algorithm may be provided for a specific temperature and a specific relative humidity of the ambient atmosphere, where the multivariate evaluation algorithm for this specific temperature and relative humidity provides a corrected value for the glucose concentration, taking into account the end value of the remission curve as a first variable $x_1$ and the (unknown) Hct of the sample. For a different temperature and/or relative humidity, a different type of multivariate evaluation algorithm may be provided. Thus, a plurality of multivariate evaluation algorithms may be stored in the evaluation device 136 and/or the evaluation unit 138, which may contain a data storage device, and may be chosen in accordance with the measured values of the temperature and/or the relative humidity, for further use.

To demonstrate the power of the multivariate correction algorithm proposed by the present disclosure, FIGS. 9 to 11B show an exemplary embodiment of a correction algorithm. For these measurements, a cNAD-based test substance was used.

Figure 9:
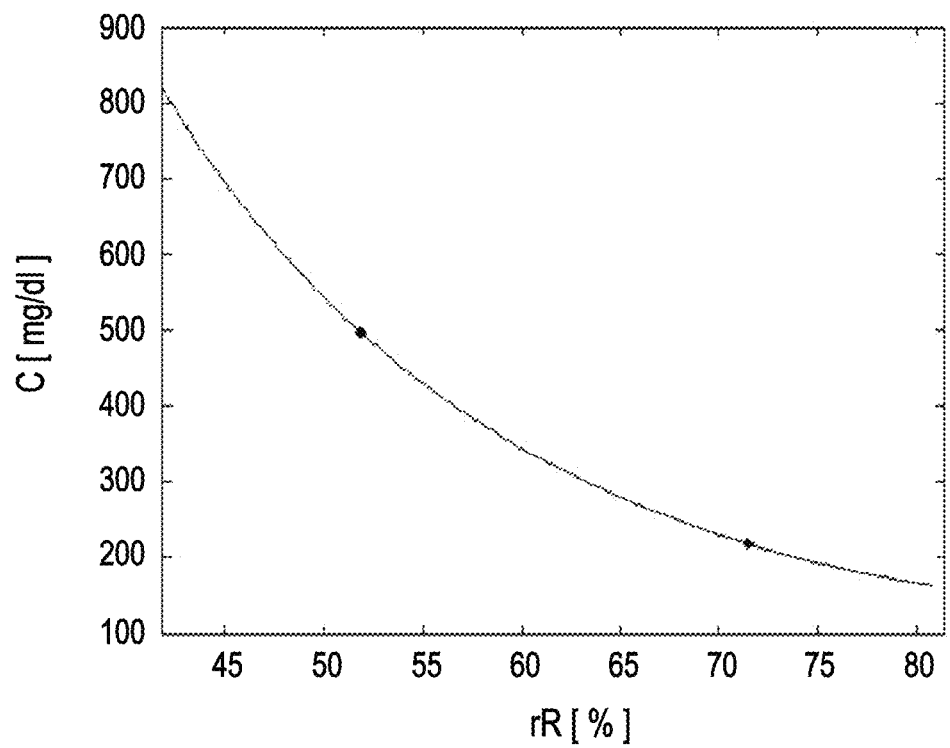
FIG. 9 shows an exemplary correlation between the end value EW or $x_1$, given as a relative remission rR in % and the glucose concentration c, for a Hct HKT 45.

Specifically, FIG. 9 shows the actual glucose concentration c, given in milligrams per deciliter, as a function of the end value of the relative remission rR, also referred to as EW or $x_1$, given in %. Further, a polynomial fit function is shown. The actual glucose concentration is determined by a laboratory method, and the relative remission is measured by taking an optical measurement curve and determining the end value of this measurement curve. The Hct for these measurements was HKT=45.

As a basis for the fit function in FIG. 9, a so-called code polynomial was used. This polynomial fit function is a univariate model that predicts the glucose concentration C as a function of the end value EW of the remission, in the following also referred to as y:

$$C(y) = c_1 + c_2 y + c_3 y^{b_1} + c_4 y^{b_2} + c_5 \exp(b_3 y).$$

In this formula, parameters $c_1, \ldots, c_5$ and $b_1, b_2, b_3$ are free parameters, which may be determined by using a calibration measurement, such as by using appropriate calibration fluid having known properties, such as a known Hct HKT45, a known glucose concentration and a known temperature. This calibration, also referred to as a generation of a code, typically is generated by using a set of data under standardized conditions, such as standard temperature, standard Hct (HKT45), standard humidity. Typically, more than two glucose concentrations can be used for calibration, such as a plurality of glucose concentrations covering the whole sensible range of glucose concentrations that might occur in practical use.

By using this fit function, the following parameters were determined for the curve shown in FIG. 9:

| | Parameter | | | | | | |
|---|---|---|---|---|---|---|---|
| $c_1$ | $c_2$ | $c_3$ | $c_4$ | $c_5$ | $b_1$ | $b_2$ | $b_3$ |
| Value $-3.51 * 10^{-4}$ | $-10.3$ | $-6.21 * 10^5$ | $0.508$ | $-2.29 * 10^{-4}$ | $-1.72$ | $1.63$ | $0.129$ |

As outlined above, the measurement of FIG. 9 was taken for one specific Hct HKT45. Thus, the algorithm is a univariate algorithm, deriving the glucose concentration from one variable (i.e., in this case the end value EW of the relative remission rR).

To derive a glucose concentration for an arbitrary Hct, the concentration c derived by the fit function formula of FIG.

9 given above as to be corrected by a correction factor K, which itself may depend on the end value EW and the at least one exponential fit parameter, such as the exponential fit parameter $\Gamma$:

$$G = G(x_1, x_2) = G(EW, \Gamma)$$
$$= C(EW, HKT45) \cdot K(EW, \Gamma).$$

Again, the correction factor K may be separated into a term that is dependent on the end value EW ($=x_1$) of the glucose concentration and a term dependent on the at least one exponential fit parameter $\Gamma$ ($=x_2$), and it may be shown that the following fit formula may be applied:

$$K(EW,\Gamma)=(\Gamma^2+a_1\cdot\Gamma+a_2)/(c_1\cdot EW^2+c_2\cdot EW+c_3).$$

This corresponds to a second end value-dependent correction of the first, $\Gamma$-dependent correction and, thus to a multivariate correction algorithm comprising the end value EW as a first variable $x_1$ and the exponential fit parameter $\Gamma$ as a second variable $x_2$. The fit function includes five independent parameters $a_1$, $a_2$ and $c_1$, $c_2$ and $c_3$. As a boundary condition, for HKT45, the correction factor shall be K=1, so the fit function of FIG. 9 is obtained as a result.

Figure 10:
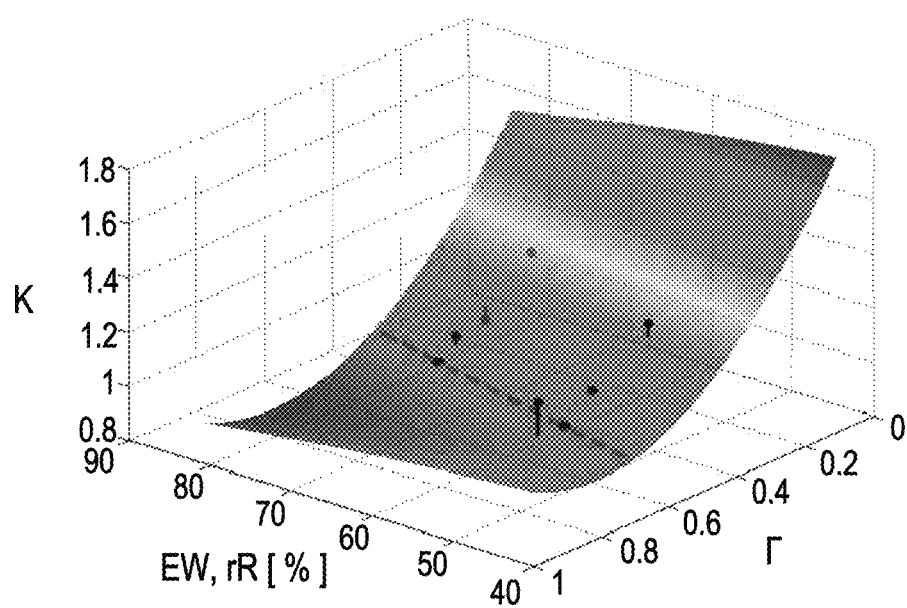
FIG. 10 shows correction factors K to be applied to the correlation, as a function of the end value EW or $x_1$, given as a relative remission rR in % and as a function of the exponential fit parameter $\Gamma$ or $x_2$.

By performing a plurality of calibration measurements for various Hcts and by determining both the end value EW as a first variable $x_1$ and the at least one exponential fit parameter $\Gamma$ as a second variable $x_2$, a three-dimensional calibration curve may be determined, which is depicted for this example in FIG. 10. The curved, shaded surface denotes the fit function of the correction factor K. For this specific example, the following fit parameters of the above-mentioned equation were determined:

| Parameter | $f_1$ | $f_2$ | $a_1$ | $a_2$ |
|---|---|---|---|---|
| Value | −0.0049 | 0.8848 | −1.5580 | 1.2048 |

Thus, a corrected glucose concentration may be determined, by using the above-mentioned multivariate correction algorithm that uses both an end value of the measurement curve and at least one exponential fit parameter as input variables.

In FIGS. 11A and 11B, corrected and uncorrected glucose concentrations are depicted for the above-mentioned measurements of FIGS. 9 and 10. FIG. 11A shows an uncorrected glucose concentration derived by using a univariate evaluation algorithm, based on the end value EW alone, as in FIG. 9, which neglects the influence of the Hct and which is based on the assumption of a Hct of HKT45. Contrarily, in FIG. 11B, results of a method as described herein, using a multivariate algorithm, specifically using the correction algorithm disclosed above in conjunction with FIG. 10, are shown. In each case, the deviation $\Delta$ is given for various actual glucose concentrations c, given in mg/dl, for various Hcts. The actual glucose concentrations were determined by using a reliable laboratory method. The deviations are given in relative units [%].

As shown by comparing FIGS. 11A and 11B, the multivariate algorithm as proposed herein significantly reduces the Hct-induced deviations. Thus, for Hcts deviating from HKT45, the errors involved by evaluating the measurement curve and determining the glucose concentration thereof may widely be lower to a level of below 10% or 10 mg/dl. Thus, even though the algorithm may be kept rather simple, the accuracy of the measurement may be induced significantly.

Figure 12:
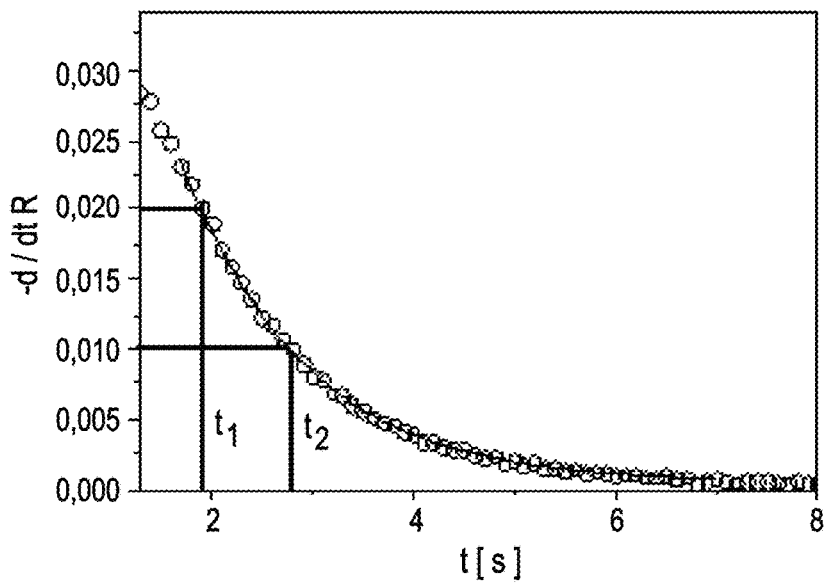
FIG. 12 shows a first order derivative of a remission of a second test substance, a fit function of the first order derivative, and two different times $t_1$ and $t_2$ at two differing threshold values.

FIG. 12 shows a first order derivative of a remission of a second test substance comprising a glucose concentration of c=446 mg/dl, a Hct of 25%, a temperature of 23° C., and a relative humidity of 45%. In addition, a fit function of the first order derivative, as well as two different times $t_1$ and $t_2$ at two differing threshold values are presented here.

The two different times $t_1$ and $t_2$ may be determined by applying the first order derivative of the remission curve that exhibits an exponential characteristic. For example, when the base line a is neglected (a=0), the first order derivative of the remission curve may, as outlined above, be described by:

$$F'(t)=b\cdot\exp(\Gamma\cdot t).$$

Inserting a first threshold $F'(t_1)$ at a time $t_1$ in a first equation, and inserting a second threshold $F'(t_2)$ at a time $t_2$, will lead to the two following different equations:

$$F'(t_1)=b\cdot\exp(\Gamma\cdot t_1);$$
$$F'(t_2)=b\cdot\exp(\Gamma\cdot t_2).$$

Applying a rearranging of the two equations and a subsequent substitution, the following equation for the decay rate $\Gamma$ of the remission curve will be acquired:

$$\Gamma=(\ln [F'(t_1)/F'(t_2)])/[t_1-t_2].$$

As an example, inserting a first value of 2%/s for the first threshold $F'(t_1)$ at a time $t_1$, and inserting a second value of 1%/s for the second threshold $F'(t_2)$ at a time $t_2$, will lead to a value of the decay rate $\Gamma$ of the remission curve as follows:

$$\Gamma=(\ln [0.01/0.02])/[t_1-t_2].$$

Taking this example into account, it is evident that determining the decay rate $\Gamma$ of the remission curve may only require that the two different times $t_1$ and $t_2$ as, for example, depicted in FIG. 12 be determined.

Figure 13:
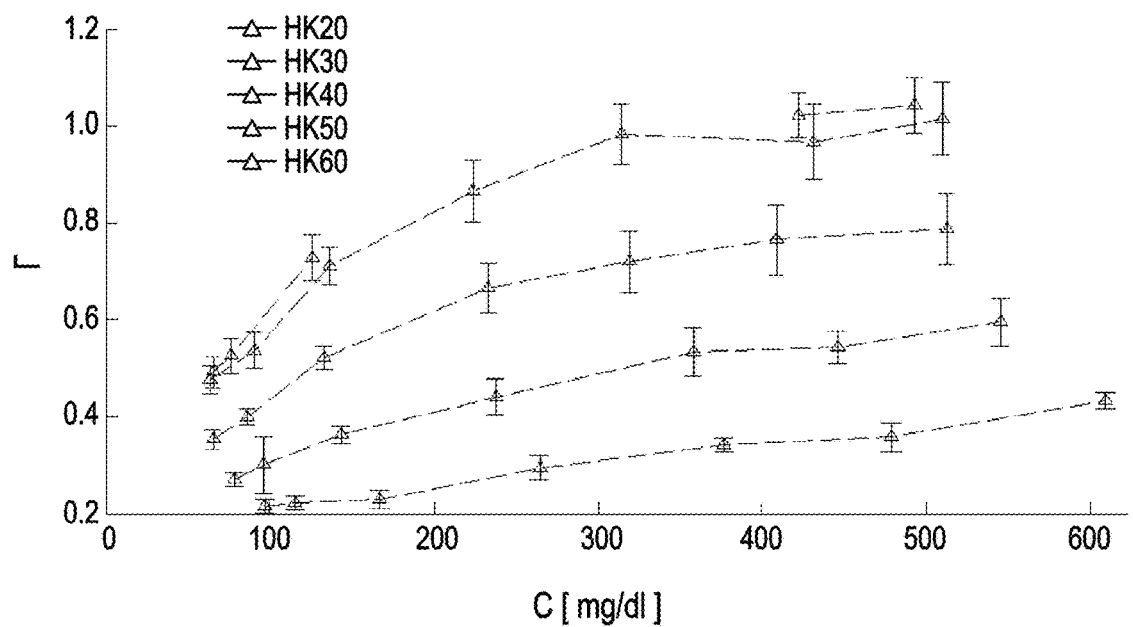
FIG. 13 shows decay rates for different Hct and glucose concentrations, where each decay constant $\Gamma$ is determined by two separate equations for the first derivative of equation (1) with neglected base line (a=0) for two differing threshold values.

In the further course, this method has been applied to a set of 10 samples of whole blood, where each sample was adjusted to one of five different Hct concentrations (e.g., 20%, 30%, 40%, 50% or 60%), as well as to one of seven different glucose concentrations within the range from 40 mg/dl to 600 mg/dl. FIG. 13 shows various decay rates $\Gamma$ of the remission curve for the different Hct and glucose concentrations, where each decay rate $\Gamma$ is determined according to the method as described in connection with FIG. 12, where a first value of −5%/s for the first threshold $F'(t_1)$ at a time $t_1$, and a second value of −2%/s for the second threshold $F'(t_2)$ at a time $t_2$ has been applied. FIG. 13 clearly shows, on one hand, a strong dependence of the decay rate $\Gamma$ from the Hct and, on the other hand, a weak dependence from the glucose concentration. The mentioned values of −5%/s for the first threshold and of −2%/s for the second threshold may be applied with regard to a glucose concentration above 70 mg/dl.

Figures 14A, 14B:
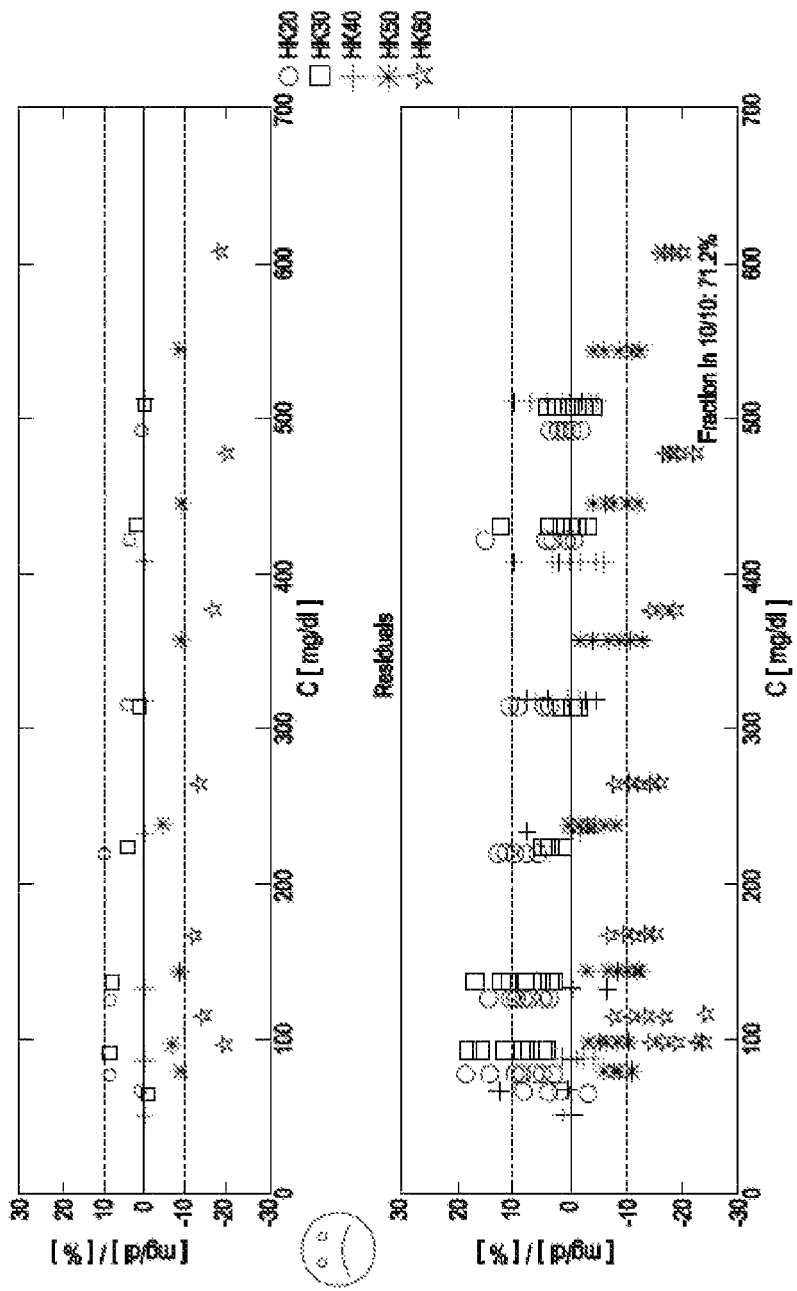
FIG. 14A shows measured glucose concentrations determined by uncorrected, univariate values as average values over 10 measured values.
FIG. 14B shows measured glucose concentrations determined by uncorrected, univariate values as single measured values.

The method described in connection with FIGS. 12 and 13 may allow determining a glucose concentration by applying a Hct correction with regard to the glucose concentration that may be acquired by using the respective threshold values. By determining glucose concentrations with a single threshold of −2%/s for the remission decay a distribution as shown in FIGS. 14A and 14B will be obtained, where 71.2% of all data points for the measured glucose values are distributed within a deviation of ±10% over the complete observed Hct range from 20% to 60%. Whereas FIG. 14A shows measured glucose concentrations as average values over 10 measured values, FIG. 14B depicts the corresponding single measured values. From FIG. 14B it may be concluded that, particularly, samples with a Hct value of 60% fall outside the desired range.

Figures 15A, 15B:
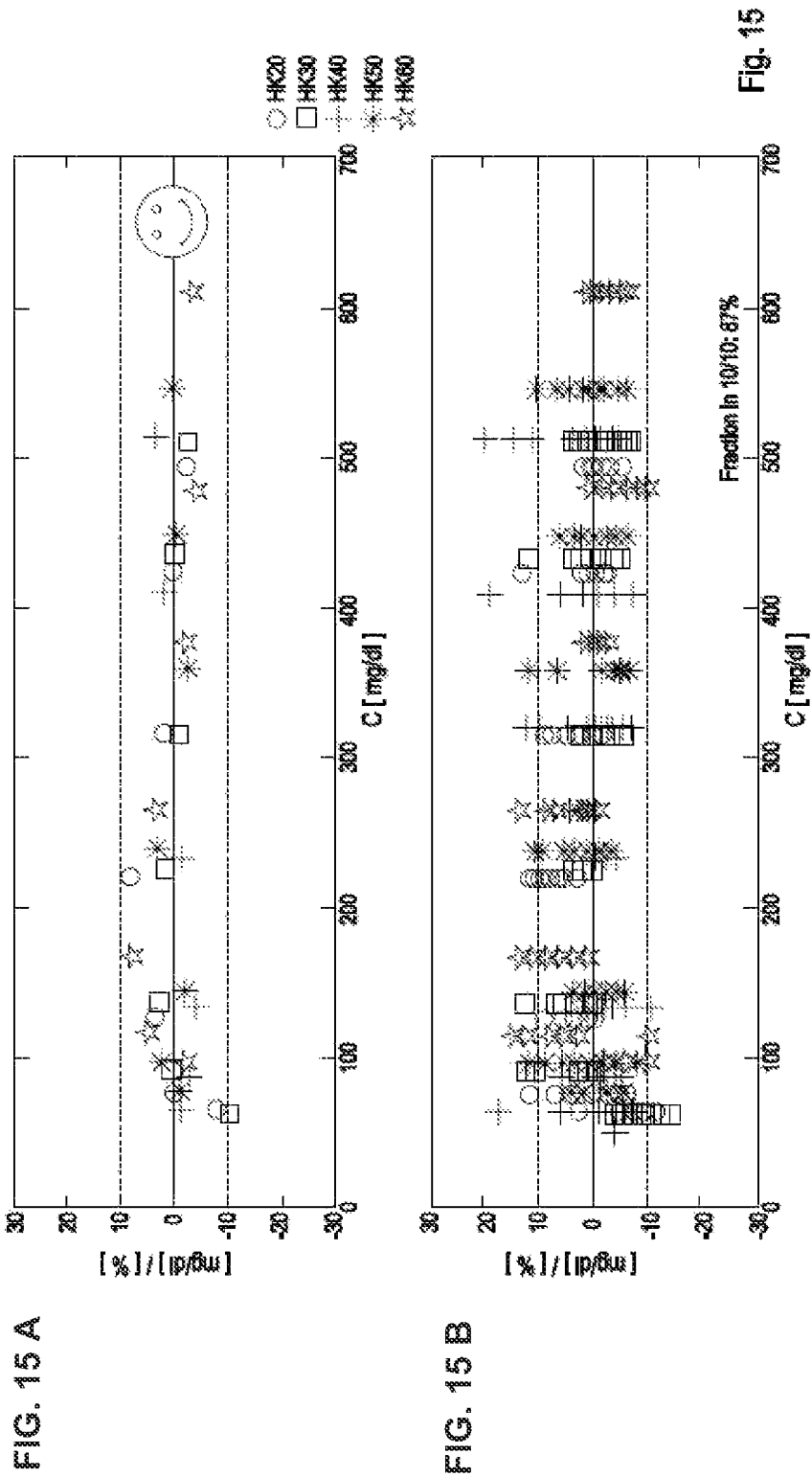
FIG. 15A shows measured glucose concentrations determined by corrected, multivariate values as average values over 10 measured values.
FIG. 15B shows measured glucose concentrations determined by corrected, multivariate values as single measured values.

In contrast to the results shown in FIGS. 14A and 14B, in the improved result shown in FIGS. 15A and 15B, 87% of all data points for the measured glucose values are distributed within a deviation of ±10% over the complete observed Hct range from 20% to 60%. This kind of improvement of more than 15% with regard to the results from FIGS. 14A and 14B may be achieved by determining the glucose concentrations using a multivariate data analysis including the decay rate Γ as determined above, for example, with the method as described in FIGS. 12 and 13. Whereas FIG. 15A shows average values over 10 measured values, FIG. 15B displays the corresponding single measured values.

However, it could have been observed that the coefficient of variation of all Hct values may increase when taking into account the Hct during the performance of the above mentioned measurements. Hereby, the coefficient of variation may be considered as a measure of a dispersion of a probability distribution of values which may be usually be defined as a ratio of the standard deviation to a mean value. This well-known effect may generally be observed during any Hct correction since no method is known so far by which the Hct may be determined exactly.

Figure 16:
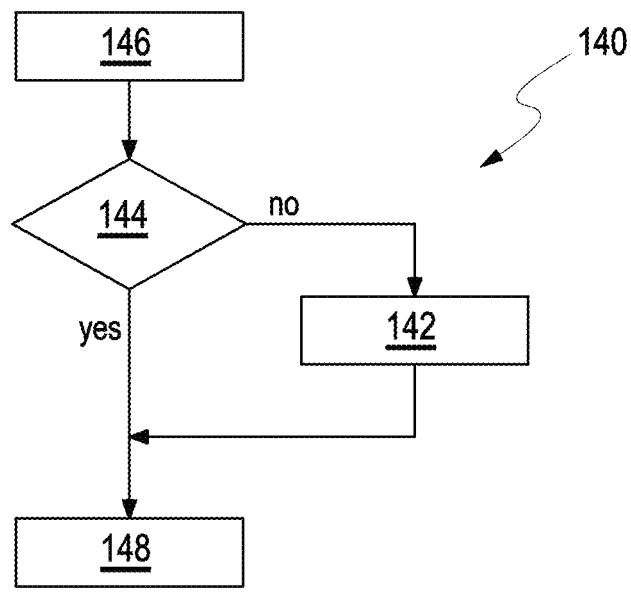
FIG. 16 shows a first decision tree, where a correction of the glucose values may only be applied outside a predetermined Hct range.

In some instances, only such glucose values may be corrected for which such a correction may be required. For example, FIG. 16 shows a first decision tree 140, where the Hct correction 142 of the glucose values may only be applied outside a predetermined Hct range 144. In particular, after a determination 146 of both the end value and the decay rate Γ, it may firstly be determined whether the Hct is inside or outside the predetermined Hct range 144, which preferably covers the range from 35% to 50%. However, other values for the predetermined Hct range 144 are possible. In this exemplary first decision tree 140, the Hct correction 142 of the glucose values may only be applied in case the Hct is outside the predetermined Hct range 144, for example, covering the range from 35% to 50%. According to this discrimination, a determination 148 of a final value for the glucose concentration may be determined with or without Hct correction 142 depending on the actual Hct value.

Consequently, the first decision tree 140, as exemplary depicted in FIG. 16, exhibits the positive effect that only such glucose values are submitted to the Hct correction 142, where the Hct correction 142 may be required for a further processing of the respective glucose values, in particular for rare cases in which a patient may display a very low or a very high Hct. Therefore, this kind of discrimination according to the first decision tree 140 may thus help to improve both the speed and the quality of the determination 148 of the final value of the glucose concentration under the influence of the Hct.

Figure 17:
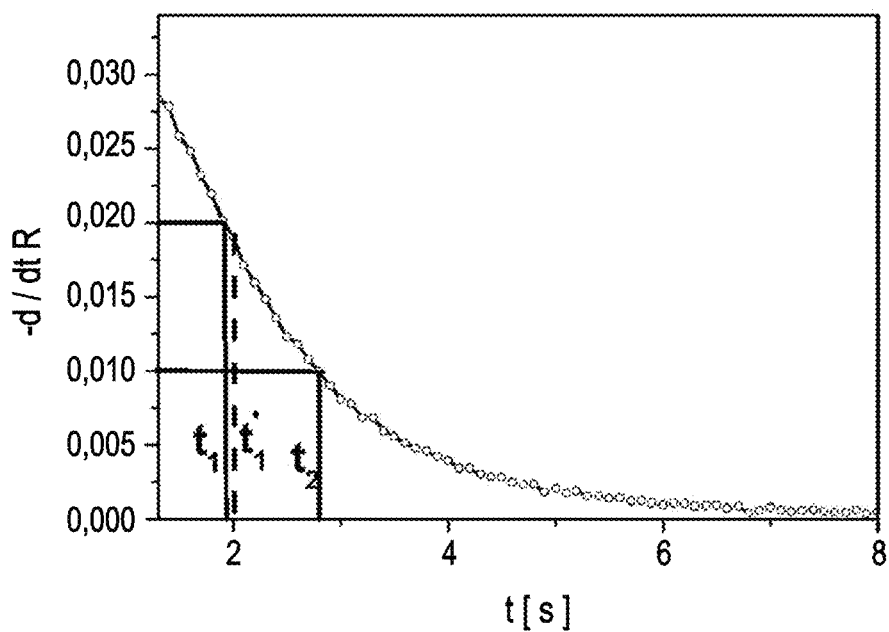
FIG. 17 shows a first order derivative of a remission of a second test substance, where the two different times $t_1$ and $t_2$ are determined by linear interpolation, whereas the time $t_1'$ is determined by the procedure as applied in FIG. 12.

In FIG. 17 a first order derivative curve of a remission curve is displayed, where the two different times $t_1$ and $t_2$ may be determined by linear interpolation of the corresponding data points before and after the respective first threshold $F'(t_1)$ at a time $t_1$ and the respective second threshold $F'(t_2)$ at a time $t_2$. This kind of procedure may be applied to determine the exact point in time at which the corresponding threshold will be achieved.

For example, at the time $t_2$, the first order derivative curve may pass through the first order derivative of an actually measured value for the respective second threshold $F'(t_2)$. In contrast with this, no such first order derivative of a measured value may exist at the corresponding first threshold $F'(t_1)$ at the time $t_1$. To solve this problem, the time $t'_1$ may be determined according to the procedure as applied in FIG. 12. However, according to FIG. 17, a linear interpolation may be performed with regard to the first derivative of two actually measured values that are in the vicinity of the first threshold $F'(t_1)$ near the time $t_1$. This procedure may be particularly useful in case of a high time resolution; otherwise it may be hard to approximate an exponential characteristic by a linear interpolation.

Figure 18:
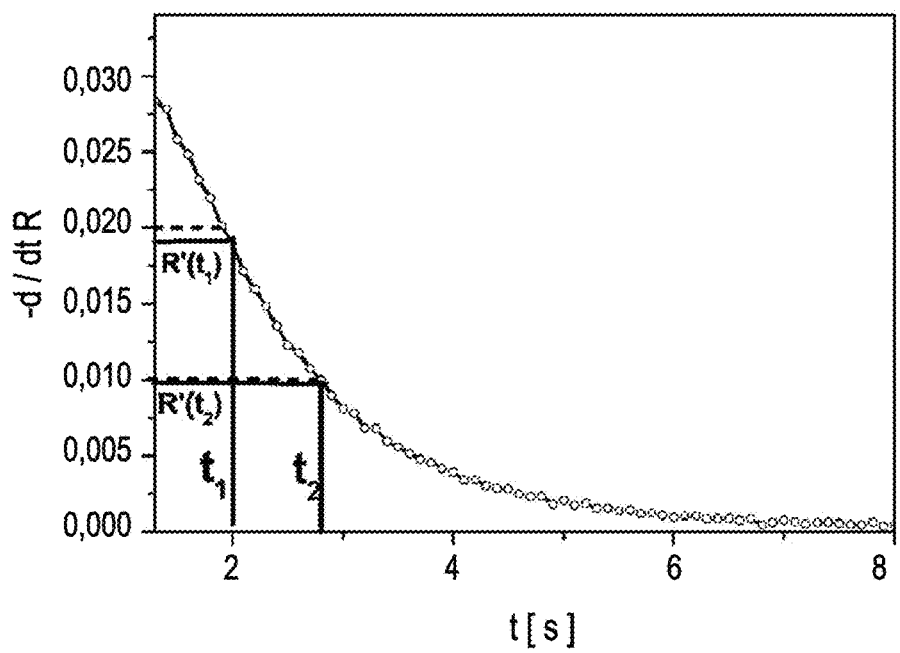
FIG. 18 shows a first order derivative of a remission of a second test substance, where the two different times $t_1$ and $t_2$ are selected from times at each of them actual values of the remission were acquired and each including the value of $R'(t_1)$ and $R'(t_2)$, respectively (i.e., the value of the first order derivative of the remission being closest to a predetermined threshold).

FIG. 18 shows an alternative approach which may, in particular, be applied in a case of a low time resolution. Starting from the equation:

$$\Gamma = (\ln [F'(t_1)/F'(t_2)])/[t_1-t_2],$$

actually determined values for a first threshold $F'(t_1)$ at a corresponding time $t_1$ as well as for the second threshold $F'(t_2)$ at a corresponding time $t_2$ are inserted into the equation, thus, leading to an exact value for the decay rate F. For example, the values for the first threshold $F'(t_1)$ and the corresponding time $t_1$ as well as the values for the second threshold $F'(t_2)$ and the corresponding time $t_2$ are determined in a manner that both values for the threshold may be the values, which are the closest to a predetermined threshold.

As described above, the decay rate Γ could only be determined for glucose concentrations above 70 mg/dl. The reason for this observed behavior may be attributed to the fact that a first threshold value of −5%/s has been applied within this kind of determination. The values of −5%/s for the first threshold and of −2%/s for the second threshold may be particularly applied since they seem to provide reasonable values for the decay rate Γ over a large range of glucose concentrations. However, this way of procedure may not be applicable to a predetermined glucose concentration range that may be of 70 mg/dl or below since a glucose concentration within this range may not achieve the value of −5%/s for the decay rate F.

Figure 19:
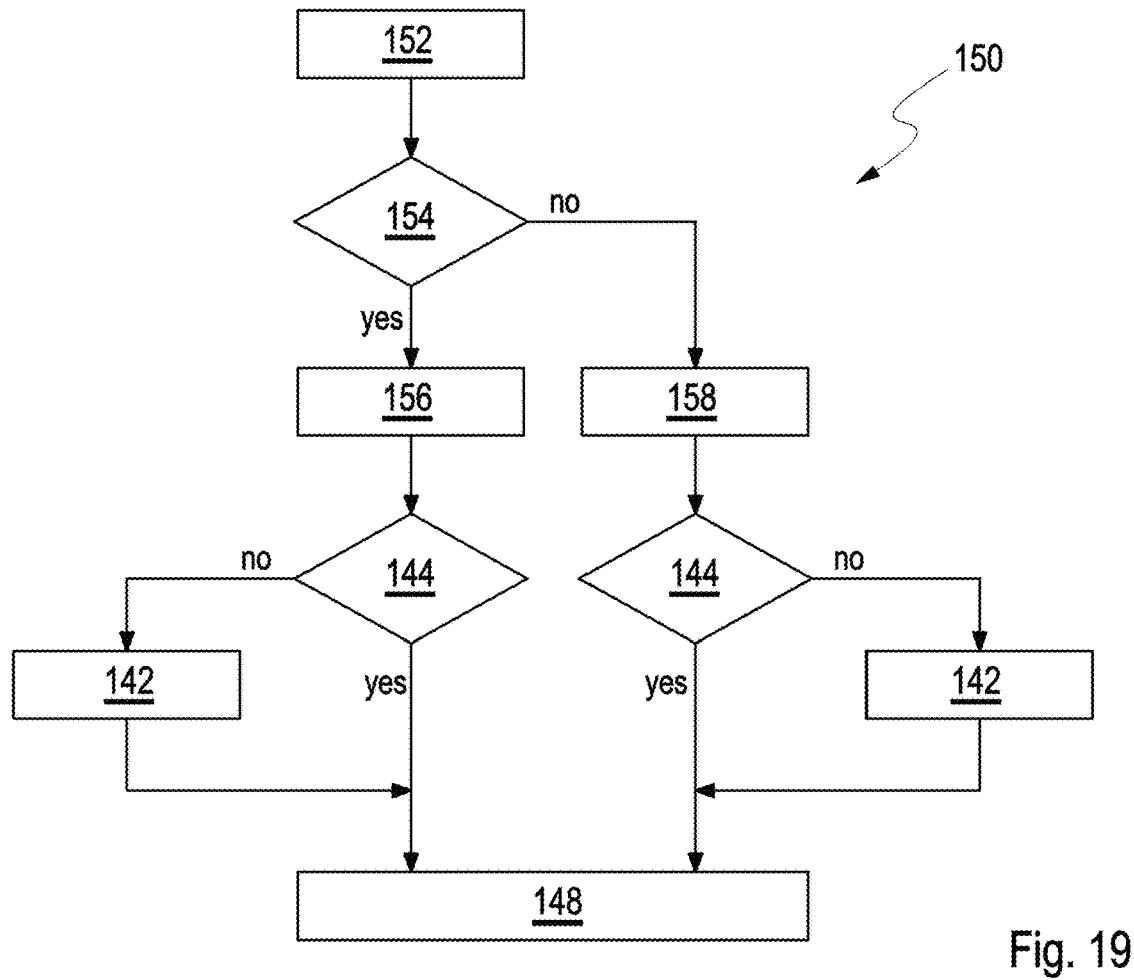
FIG. 19 shows a second decision tree, where firstly, respective threshold values for determining the glucose concentration may be selected according to a predetermined glucose concentration range, and where secondly, a correction of the glucose values may only be applied outside the predetermined Hct range.

Consequently, the determination 148 of the final value of the glucose concentration may be performed according to a second decision tree 150 as exemplary depicted in FIG. 19.

According to the second decision tree 150, the method may start with a determination 152 of the final value, from which a preliminary value for the glucose concentration may be derived. According to whether the preliminary value for the glucose concentration falls within a predetermined glucose concentration range 152, firstly, respective first and second threshold values 156, 158 for determining the actual glucose concentration may be selected. In this example, in case the preliminary value for the glucose concentration may be estimated to be below 100 mg/dl, first and second threshold values 156 of −2%/s for the first threshold and of −0.5%/s for the second threshold may be particularly applied, whereas in case the preliminary value for the glucose concentration may be estimated to be 100 mg/dl or more, the above mentioned values of −5%/s and of −2%/s may be selected as first and second threshold values 158. However, other values the first threshold and for the second threshold may be chosen.

Secondly, in an additional second-order decision branch of the second decision tree 150, a Hct correction 142 of the glucose values may only be applied outside the predetermined Hct range 144. As already described above in relation to FIG. 16, the Hct correction 142 of the glucose values may only be performed in case the Hct takes a value outside a range of 35% to 50%. However, other values are possible. According to the discrimination as depicted in FIG. 19, the determination 148 of a final value for the glucose concentration may be determined here also with or without Hct correction 142 depending on the actual value of the Hct. Hereby, the actual values chosen for the Hct correction 142 may be independent from the second-order decision branch of the second decision tree 150. Alternatively, for the Hct correction 142 actual values may be chosen that might depend on which second-order decision branch of the second decision tree 150 the Hct correction 142 may be performed.

Consequently, the second decision tree 150 as exemplary depicted in FIG. 19 exhibits the positive effects that, firstly, very low glucose values even down to 40 mg/dl or below may be correctly determine, and that, secondly, only such glucose values are submitted to the Hct correction 142 where it may be required in particular for rare cases in which a patient may display a very low or a very high Hct. Therefore, this kind of discrimination according to the second decision tree 150 may thus help to improve both the speed and the quality of the determination 148 of the final value of the glucose concentration over a much larger range of glucose concentrations than before, thereby being able to taking into account the Hct for a correction of the glucose concentration. Alternatively or in addition, a weighted average may be employed within the method of analyzing the body fluid sample for taking into account a number of glucose concentrations measured on variations of the Hct, which may be considered as the disturbance variable Y, to derive the averaged concentration $\overline{c_{ave}}$ of the analyte:

$$\overline{c_{ave}} = \Sigma_{i=1}^{n} p_i \cdot c^i$$

or $$\overline{c_{ave}} = (\Sigma_{i=1}^{n} p_i \cdot c^i)/(\Sigma_{i=1}^{n} p_i).$$

Herein, the weighted average $\overline{c_{ave}}$ may include weights $p_i$ that may denote probabilities for each specific value $C^i$ of the Hct according to a forecast model that may reflect the probability distribution of each specific value of the disturbance variable Y.

Figure 20:
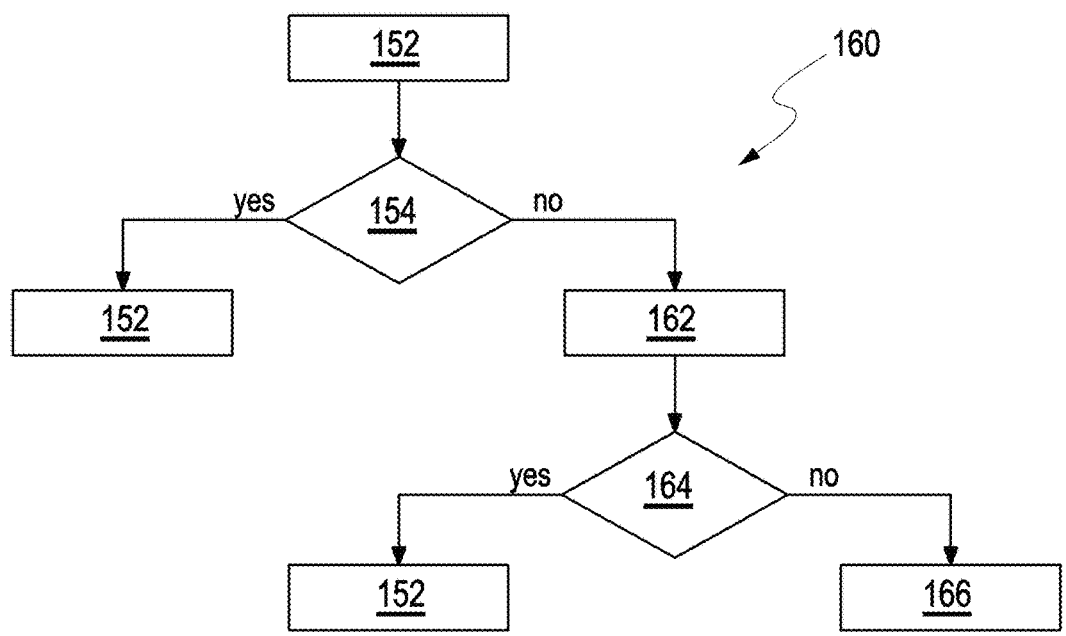
FIG. 20 shows a third decision tree, where firstly, depending on whether the glucose concentration may be within a predetermined glucose concentration range, the decay constant $\Gamma$ may be taken into account when determining the glucose concentration, and, secondly, depending on whether the decay constant $\Gamma$ may be equal to or exceed a predefined constant $\Gamma_0$, the Hct may be taken into account.

As a further example, FIG. 20 shows a third decision tree 160, where from the determination 152 of the end value the preliminary value for the glucose concentration may be derived. According to an assessment whether the preliminary value for the glucose concentration may fall within the predetermined glucose concentration range 154, the preliminary value for the glucose concentration as acquired by the determination 152 of the end value may be kept or not. In the latter case, a determination 162 of the decay constant $\Gamma$ or the quantity related to the decay constant $\Gamma$, such as a quantity proportional to the decay constant $\Gamma$ or proportional to the inverse $1/\Gamma$ of the decay constant, may be performed. According to a further assessment 164 that might deliver an answer to the question whether the decay constant $\Gamma$ or the quantity related to the decay constant $\Gamma$ may be equal to or exceed a predefined constant $\Gamma_0$, the preliminary value for the glucose concentration as acquired by the determination 152 of the end value may still be kept or not. In the latter case, an additional evaluation procedure 166 for determining the glucose concentration may be performed, where the additional evaluation procedure 166 may take the Hct into account. Herein, the additional evaluation procedure 166 may further include another decision branch (not depicted here) that might branch out to different Hct evaluation procedures depending on whether the decay constant $\Gamma$ or the quantity related to the decay constant $\Gamma$ may be equal to or exceed a further predefined constant $\Gamma_1$. Thereby, a weighted average as described above may be employed within at least one of the different Hct evaluation procedures.

Figure 21:
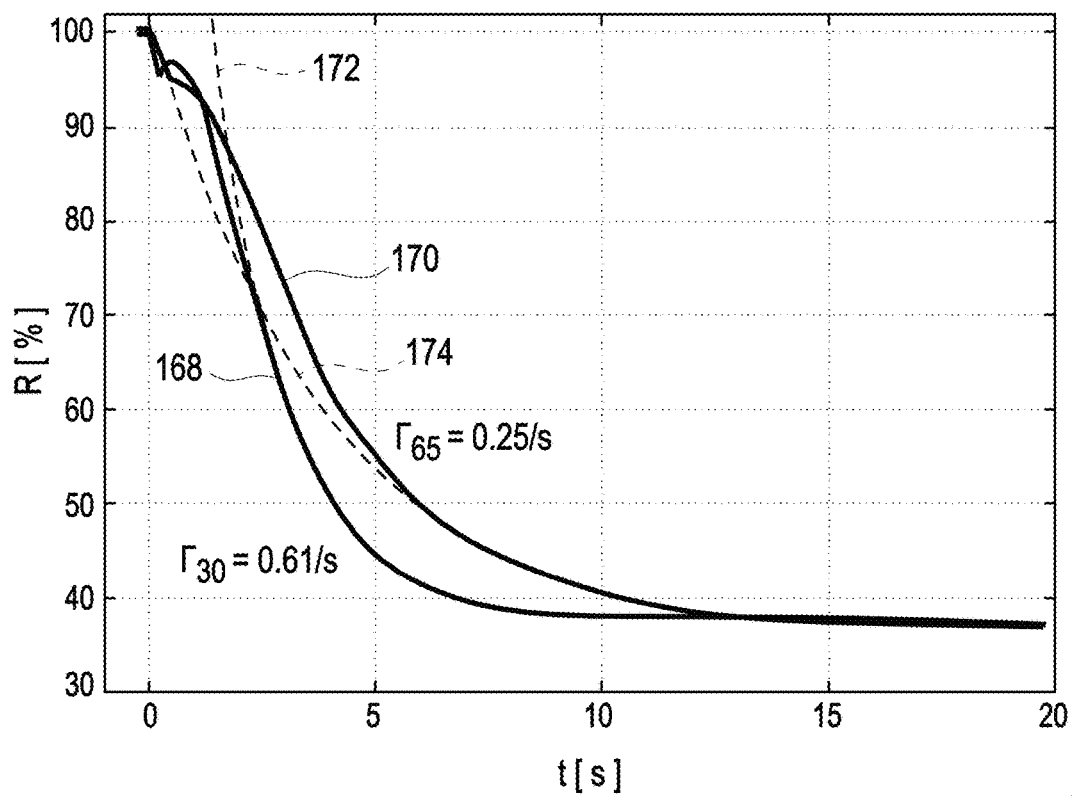
FIG. 21 shows two typical measurement curves of the relative remission, where the two curves are distinguished from each other by Hct, and two respective exponential fits for the corresponding Hct.

This kind of decision tree, in particular the third decision tree 160 as schematically presented in FIG. 20, may be employed for an evaluation of measurement curves as depicted in FIG. 21. As a typical example, FIG. 21 shows two measurement curves of the time dependence in s of the relative remission indicating the progress of the respective detection reactions of two blood samples each including a specific amount of glucose. Herein, both remission curves were derived by using a modified PQQ chemistry, where the usual PQQ chemistry was modified by employing an enzyme mutant. As depicted from FIG. 20, the two remission curves are distinguished from each other by their respective amount of Hct. While a first measurement curve 168, being over most of the time, particularly within the evaluation part of the measurement curve, the lower curve, was recorded under a Hct of 30%, a second measurement curve 170, being over most of the time, particularly within the evaluation part of the measurement curve, the upper curve, was recorded under a Hct of 65%.

As further shown in FIG. 21, both measurement curves 168, 170 could, particularly within the evaluation part of the measurement curve, be fitted by two respective exponential fits 172, 174. This feature particularly relates to the evaluation part of the measurement curve exhibiting here an exponential characteristic and, by successfully allowing this kind of procedure, additionally proves this fact. Consequently, the first measurement curve 168 could, within the evaluation part of the measurement curve, be fitted by a first exponential fit 172, thereby providing a value of 0.61/s for the decay constant r, while the second measurement curve 168 could, also within the evaluation part of the measurement curve, be fitted by a second exponential fit 172, thereby providing a value of 0.25/s for the decay constant $\Gamma$. This example, as depicted in FIG. 21, clearly demonstrates which kind of decisive impact the Hct may exert on the remission of blood samples, leading to a conclusion that, at least in some cases, inaccurate results for the glucose concentration may be acquired as long as the influence of the Hct might be not adequately taken in to account or even completely neglected. This situation which had been difficult to tackle so far may now be properly dealt with by applying the methods here.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

NUMBERED EMBODIMENTS

Embodiment 1

A method for analyzing at least one sample of a body fluid, the method comprising the following steps:

a). recording a plurality of measurement values by monitoring a time development of at least one measurement value indicating a progress of a detection reaction of at least one test substance and the sample of the body fluid, and providing at least one measurement curve F(t) which contains the measurement values, wherein at least an evaluation part of the measurement curve has an exponential characteristic, wherein the measurement values contained in the measurement curve are acquired at differing points in time, wherein the detection reaction is known to be influenced by a concentration c of an analyte to be detected in the body fluid and at least one disturbance variable Y;

b). deriving an end value of the measurement curve, wherein the end value forms a first variable $x_1$;

c). deriving at least one fit parameter from the measurement curve by taking into account the exponential characteristic of at least the evaluation part of the measurement curve, wherein the fit parameter forms at least one second variable $x_2$;

d). deriving the concentration c of the analyte by using at least one multivariate evaluation algorithm, the multivariate evaluation algorithm being adapted to combine the first variable $x_1$ and the second variable $x_2$.

Embodiment 2

A method for analyzing at least one sample of a body fluid, the method comprising the following steps:

a') providing at least one measurement curve F(t), wherein the measurement curve contains a plurality of measurement values recorded by monitoring a time development of at least one measurement value indicating a progress of a detection reaction of at least one test substance and the sample of the body fluid, wherein the measurement values contained in the measurement curve are acquired at differing points in time, wherein the detection reaction is known to be influenced by a concentration c of an analyte to be detected in the body fluid and at least one disturbance variable Y;

b') deriving an end value of the measurement curve, wherein the end value forms a first variable $x_1$;

c') deriving at least one fit parameter from the measurement curve by assuming an exponential characteristic of at least an evaluation part of the measurement curve, wherein the fit parameter forms at least one second variable $x_2$;

d') deriving the concentration c of the analyte by using at least one multivariate evaluation algorithm, the multivariate evaluation algorithm being adapted to combine the first variable $x_1$ and the second variable $x_2$.

Embodiment 3

The method according to any one the preceding embodiments, wherein the body fluid is selected from the group consisting of blood and interstitial fluid.

Embodiment 4

The method according to any one of the preceding embodiments, wherein the analyte is glucose.

Embodiment 5

The method according to any one of the preceding embodiments, wherein the test substance contains at least one enzyme, preferably GOD and/or GDH.

Embodiment 6

The method according to any one of the preceding embodiments, wherein the measurement values are optical measurement values.

Embodiment 7

The method according to the preceding embodiment, wherein the optical measurement values are detected by a reflective measurement.

Embodiment 8

The method according to any one of the two preceding embodiments, wherein the measurement values are remission values.

Embodiment 9

The method according to one of the preceding embodiments, wherein the disturbance variable Y comprises a parameter which is able to influence the viscosity of the body fluid.

Embodiment 10

The method according to one of the preceding embodiments, wherein the at least one disturbance variable is selected from the group consisting of: a particulate content of the sample, preferably a hematocrit; a temperature of the sample.

Embodiment 11

The method according to any one of the preceding embodiments, wherein the exponential characteristic contains at least one exponential function selected from the group consisting of:

$$F(t)=a+b*\exp[-\Gamma*t],$$

wherein t is the time, a is an offset, b is a contrast and r is a decay constant;

$$F(t)=a+b*\exp[-(\Gamma*t)^\beta],$$

wherein t is the time, a is an offset, b is a contrast, r is a decay constant and β is a stretching parameter.

Embodiment 12

The method according to the preceding embodiment, wherein the second variable $x_2$ is selected from the decay constant Γ or from a quantity which is in relationship with the decay constant Γ.

Embodiment 13

The method according to the preceding embodiment, wherein the quantity is proportional to the decay constant Γ or proportional to the inverse 1/Γ of the decay constant.

Embodiment 14

The method according to any one of the preceding embodiments, wherein, in step c), a first order derivative F'(t) or a higher order derivative F''(t) of the measurement curve is formed before deriving the fit parameter.

Embodiment 15

The method according to the preceding embodiment, wherein the measurement values of the measurement curve are acquired equally spaced in time.

Embodiment 16

The method according to the preceding embodiment, wherein the measurement curve is acquired at a constant measurement frequency of 10 Hz to 100 Hz.

Embodiment 17

The method according to any one of the two preceding embodiments, wherein the first or higher order derivative is approximated by calculating differences between neighboring measurement values.

Embodiment 18

The method according to any one of the preceding embodiments, wherein, in step c), a ratio of two subsequent derivatives $F''(t)$ and $F''^{+1}(t)$ of the measurement curve is formed, the ratio forming the fit parameter.

Embodiment 19

The method according to any one of the preceding embodiments, wherein, in step c), an integral is formed over the measurement curve $F(t)$ or a first order or higher order derivative of $F(t)$, the integral forming the fit parameter.

Embodiment 20

The method according to any one of the preceding embodiments, wherein, in step c), the fit parameter is obtained from a comparison of a first order derivative of the measurement curve at two differing points in time.

Embodiment 21

The method according to the preceding embodiment, wherein the two differing points in time are obtained by applying two differing threshold values.

Embodiment 22

The method according to the pre-preceding embodiment, wherein at least one of the two differing points in time is obtained by a linear interpolation between two differing values which 1 are in the vicinity of a threshold value.

Embodiment 23

The method according to the pre-pre-preceding embodiment, wherein two differing values for the two differing points in time are used, wherein each of the two differing values are in the vicinity of a threshold value.

Embodiment 24

The method according to any one of the three preceding embodiments, wherein the two differing threshold values are selected from a range from −10%/s to −0.1%/s.

Embodiment 25

The method according to the preceding embodiment, wherein the two differing threshold values are selected from a range from −5%/s to −2%/s.

Embodiment 26

The method according to any one of the five preceding embodiments, wherein the two differing threshold values are selected according to a preliminary estimation of the body fluid concentration.

Embodiment 27

The method according to the preceding embodiment, wherein the body fluid comprises glucose, wherein the preliminary estimation of the body fluid concentration leads to a value of or above 100 mg/dl, and wherein the two differing threshold values selected are as −5%/s and −2%/s.

Embodiment 28

The method according to the pre-preceding embodiment, wherein the body fluid comprises glucose, wherein the preliminary estimation of the glucose concentration leads to a value below 100 mg/dl, and wherein the two differing threshold values selected are −2%/s and −0.5%/s.

Embodiment 29

The method according to any one of the preceding embodiments, wherein the body fluid comprises glucose, and wherein a hematocrit correction is applied to the glucose concentration.

Embodiment 30

The method according to the preceding embodiment, wherein the hematocrit correction is applied to the glucose concentration in case the hematocrit is outside a predetermined hematocrit range.

Embodiment 31

The method according to the preceding embodiment, wherein the predetermined hematocrit range comprises hematocrit values from 35% to 50%.

Embodiment 32

The method according to any one of the preceding embodiments, wherein, in step d), further the at least one disturbance variable Y is determined.

Embodiment 33

The method according to any one of the preceding embodiments, wherein, in step d), a weighted average of results of at least two procedures based on variations of the at least one disturbance variable Y are provided to derive a value for the concentration c of the analyte.

Embodiment 34

The method according to the preceding embodiment, wherein the weighted average comprises weights which denote probabilities for each specific value of the at least one disturbance variable Y.

Embodiment 35

The method according to the preceding embodiment, wherein a forecast model provides a probability distribution of each specific value of the at least one disturbance variable Y.

Embodiment 36

The method according to any one of the preceding embodiments, wherein, in step b), a slope of the measurement curve is compared to at least one threshold value for determining if the measurement curve has reached the end value.

Embodiment 37

The method according to the preceding embodiment, wherein difference values of neighboring measurement values of the measurement curve are formed and compared to the at least one threshold value.

Embodiment 38

The method according to any one of the preceding embodiments, wherein, in step b), the end value is derived from at least one measurement value of the measurement curve and, in step c), the at least one second variable is derived from at least one fit parameter from the measurement curve.

Embodiment 39

The method according to any one of the preceding embodiments, wherein, in step b), the end value is derived from an earlier part of the measurement curve, wherein the earlier part is a part of the measurement curve being distant from a plateau of the measurement curve.

Embodiment 40

The method according to the preceding embodiment, wherein every measurement curve may form a same plateau value independent from the at least one disturbance variable Y.

Embodiment 41

The method according to any of the two preceding embodiments, wherein the end value may be determined from the same part of the measurement curve in which the decay constant $\Gamma$ or a quantity related to the decay constant $\Gamma$ may be determined as the second variable $x_2$.

Embodiment 42

The method according to any one of the preceding embodiments, wherein the evaluation part of the measurement curve is a remainder of the measurement curve starting after a definable starting time span after a commencement of a measurement.

Embodiment 43

The method according to the preceding embodiment, wherein the starting time span is a predetermined time span.

Embodiment 44

The method according to the preceding embodiment, wherein the predetermined time span is 0.5 s to 3 s, preferably 1.0 s to 2.0 s and most preferably 1.5 s to 1.7 s.

Embodiment 45

The method according to any one of the preceding embodiments, wherein the multivariate evaluation algorithm is determined by using a plurality of calibration measurements.

Embodiment 46

A computer program including computer-executable instructions for performing the method according to any one of the preceding embodiments when the program is executed on a computer or computer network.

Embodiment 47

An evaluation device for analyzing at least one sample of a body fluid, the evaluation device comprising at least one evaluation unit, wherein the evaluation unit is adapted to perform the method according to one of the preceding embodiments referring to a method for analyzing at least one sample of a body fluid.

Embodiment 48

A sample analysis device for analyzing a sample of a body fluid, the device comprising:
at least one measuring unit for measuring a detection reaction of at least one test substance and at least one sample of a body fluid, wherein the detection reaction is known to be influenced by a set of disturbance variables, each disturbance variable characterizing at least one of a state of the sample of the body fluid and a condition of the detection reaction, the measuring unit further being adapted for monitoring a time development of at least one measurement value indicating a progress of the detection reaction, thereby recording a measurement curve F(t) containing a plurality of the measurement values acquired at different points in time, wherein at least an evaluation part of the measurement curve has an exponential characteristic; and
at least one evaluation device according to the preceding embodiment.

Embodiment 49

The sample analysis device according to the preceding embodiment, furthermore comprising at least one test element, preferably at least one test strip, wherein the test element contains the at least one test substance adapted to perform the detection reaction, wherein the sample analysis device is adapted such that the sample of the body fluid is applicable to the test element.

Embodiment 50

The sample analysis device according to one of the two preceding embodiments, wherein the sample analysis device is embodied as a hand-held device

LISTING OF REFERENCE NUMBERS 110 sample analysis device
112 hand-held device 114 casing
116 display
118 control
120 data interface
122 test element
124 test field
126 test substance
128 measuring unit
130 detector
132 light source
134 light-sensitive element
136 evaluation device
138 evaluation unit
140 first decision tree
142 hematocrit correction
144 predetermined hematocrit range
146 determination of the end value and the decay rate
148 final determination of the value of the glucose concentration
150 second decision tree
152 determination of the end value
154 predetermined glucose concentration range
156 first and second threshold values determining the actual glucose concentration
158 first and second threshold values determining the actual glucose concentration
160 third decision tree
162 determination of decay constant
164 further assessment
166 additional evaluation procedure
168 first measurement curve
170 second measurement curve
172 first exponential fit
174 second exponential fit

The invention claimed is:

1. A computer-implemented method for analysis of at least one sample of a body fluid, the body fluid comprising at least one analyte, by which analysis a concentration c of the analyte is derived, the method comprising the following steps:
a) using a detector to obtain a plurality of measurement values derived from a detection reaction created by contacting at least one sample of a body fluid from a subject with at least one test substance wherein the detection reaction is influenced by a concentration c of an analyte to be detected and at least one disturbance variable Y in the at least one sample of the body fluid, the detection reaction detected by the detector, the detector in communication with an analytic computer comprising a processor and a memory;
b) using the processor configured to analyze the at least one sample of the body fluid by the following steps:
recording at the memory, the plurality of measurement values by monitoring a time development of at least one measurement value indicating a progress of the detection reaction of the at least one test substance and the at least one sample of the body fluid, and providing at least one measurement curve F(t) which contains the time development of the plurality of the measurement values, wherein the measurement values contained in the measurement curve are acquired at differing points in time, wherein the measurement curve has at least one evaluation part having an exponential characteristic,
wherein the detection reaction is influenced by a concentration c of an analyte to be detected in the at least one sample of the body fluid and at least one disturbance variable Y, and wherein the processor includes one or more software components configured to record the plurality of measurement values by
c) deriving an end value of the measurement curve provided in step b), wherein the end value forms a first variable x1;
d) deriving at least one fit parameter from the measurement curve provided in step b) by taking into account the exponential characteristic of at least the evaluation part of the measurement curve, wherein the fit parameter forms at least one second variable x2; and
e) deriving the concentration c of the analyte by using at least one multivariate evaluation algorithm, the multivariate evaluation algorithm combining the first variable x1 provided by step c) and the second variable x2 provided by step d).

2. The method of claim 1, wherein the measurement values are optical measurement values.

3. The method of claim 1, wherein the disturbance variable Y comprises a parameter which is able to influence the viscosity of the body fluid.

4. The method of claim 1, wherein the at least one disturbance variable is selected from the group consisting of: a particulate content of the sample and a temperature of the sample.

5. The method of claim 4, wherein the particulate content of the sample comprises a hematocrit.

6. The method of claim 1, wherein the exponential characteristic contains at least one exponential function selected from the group consisting of:
$F(t)=a+b*\exp[-\Gamma*t]$, wherein t is the time, a is an offset, b is a contrast and $\Gamma$ is a decay constant;
$F(t)=a+b*\exp[-(\Gamma*t)^\beta]$, wherein t is the time, a is an offset, b is a contrast, $\Gamma$ is a decay constant and $\beta$ is a stretching parameter.

7. The method of claim 1, wherein the second variable $x_2$ is selected from the decay constant $\Gamma$ or from a quantity which is in relationship with the decay constant $\Gamma$.

8. The method of claim 1, wherein, in step d), a first order derivative F'(t) or a higher order derivative Fn(t) of the measurement curve is formed before deriving the fit parameter.

9. The method of claim 8, wherein the first or higher order derivative is approximated by calculating differences between neighboring measurement values.

10. The method of claim 1, wherein, in step d), a ratio of two subsequent derivatives $F''(t)$ and $F^{n+1}(t)$ of the measurement curve is formed, the ratio forming the fit parameter.

11. The method of claim 1, wherein, in step d), an integral is formed over the measurement curve F(t) or a first order or higher order derivative of F(t), the integral forming the fit parameter.

12. The method of claim 1, wherein, in step d), the fit parameter is obtained from a comparison of the first order derivative of the measurement curve at two differing points in time.

13. The method of claim 12, wherein the two differing points in time are obtained by applying two differing threshold values.

14. The method of claim 12, wherein two differing values for the two differing points in time are used, wherein each of the two differing values are in the vicinity of a threshold value.

15. The method of claim 1, wherein, in step e), further the at least one disturbance variable Y is determined.

16. The method of claim 1, wherein, in step b), a slope of the measurement curve is compared to at least one threshold value for determining if the measurement curve has reached the end value.

17. The method of claim 1, wherein, in step c), the end value is derived from at least one measurement value of the measurement curve and, in step d), the at least one second variable is derived from at least one fit parameter from the measurement curve.

18. The method of claim 1, wherein, in step c), the end value is derived from an earlier part of the measurement curve, wherein the earlier part is a part of the measurement curve being distant from a plateau of the measurement curve.

19. The method of claim 1, wherein the evaluation part of the measurement curve is a remainder of the measurement curve starting after a definable starting time span after a commencement of a measurement.

20. The method of claim 1, wherein the multivariate evaluation algorithm is determined by using a plurality of calibration measurements.

21. An evaluation device for analyzing at least one sample of a body fluid, the evaluation device comprising at least one evaluation unit in communication with a processor configured to perform a method for analysis of at least one sample of a body fluid, the body fluid comprising at least one analyte, by which analysis a concentration c of the analyte is derived, the method comprising:

a) using a detector to obtain a plurality of measurement values derived from a detection reaction created by contacting at least one sample of a body fluid from a subject with at least one test substance wherein the detection reaction is influenced by a concentration c of an analyte to be detected and at least one disturbance variable Y in the at least one sample of the body fluid, the detection reaction detected by the detector, the detector in communication with an analytic computer comprising the processor and a memory;

b) using the processor configured to analyze the at least one sample of the body fluid by the following steps:
recording at the memory, the plurality of measurement values by monitoring a time development of at least one measurement value indicating a progress of the detection reaction of the at least one test substance and the at least one sample of the body fluid, and providing at least one measurement curve F(t) which contains the time development of the plurality of the measurement values, wherein the measurement values contained in the measurement curve are acquired at differing points in time, wherein the measurement curve has at least one evaluation part having an exponential characteristic, wherein the detection reaction is influenced by a concentration c of an analyte to be detected in the at least one sample of the body fluid and at least one disturbance variable Y, and wherein the processor includes one or more software components configured to record the plurality of measurement values by c) deriving an end value of the measurement curve provided in step b), wherein the end value forms a first variable $x_1$;

d) deriving at least one fit parameter from the measurement curve provided in step b) by taking into account the exponential characteristic of at least the evaluation part of the measurement curve, wherein the fit parameter forms at least one second variable $x_2$; and e) deriving the concentration c of the analyte by using at least one multivariate evaluation algorithm, the multivariate evaluation algorithm combining the first variable $x_1$ provided by step c) and the second variable $x_2$ provided by step d).

* * * * *